United States Patent [19]
Beschorner

[11] Patent Number: 6,060,049
[45] Date of Patent: May 9, 2000

[54] SURROGATE TOLEROGENESIS FOR THE DEVELOPMENT OF TOLERANCE TO XENOGRAFTS

[75] Inventor: William E. Beschorner, Baldwin, Md.

[73] Assignee: Ximerex, Inc., Omaha, Nebr.

[21] Appl. No.: 08/295,899

[22] PCT Filed: May 24, 1994

[86] PCT No.: PCT/US94/05844

§ 371 Date: Jun. 6, 1995

§ 102(e) Date: Jun. 6, 1995

[87] PCT Pub. No.: WO94/27622

PCT Pub. Date: Dec. 8, 1993

Related U.S. Application Data

[63] Continuation of application No. 08/065,370, May 24, 1993.

[51] Int. Cl.$^7$ ............. A61K 48/00; C12N 15/00; A01N 1/02

[52] U.S. Cl. ............. 424/93.21; 424/93.3; 424/577; 800/8; 435/1.1

[58] Field of Search ................. 424/529, 577, 424/93.7, 93.21, 93.71, 2, 9, 93.3; 435/1, 240.2, 375, 377; 800/DIG. 5, 2, 8

[56] References Cited

U.S. PATENT DOCUMENTS

| | | |
|---|---|---|
| 4,400,376 | 8/1983 | Sanderson . |
| 4,406,885 | 9/1983 | Pinter . |
| 4,448,765 | 5/1984 | Ash et al. . |
| 4,624,917 | 11/1986 | Sugimoto . |
| 5,004,681 | 4/1991 | Boyse et al. . |
| 5,061,620 | 10/1991 | Tsukamoto et al. . |

FOREIGN PATENT DOCUMENTS

| | | |
|---|---|---|
| 63/39820 | 2/1988 | Japan . |
| 63/170322 | 7/1988 | Japan . |
| 1/26519 | 1/1989 | Japan . |
| 1/132528 | 5/1989 | Japan . |
| WO/91/18615 | 12/1991 | WIPO . |
| WO 93/09234 | 5/1993 | WIPO ............... C12N 15/19 |

OTHER PUBLICATIONS

Herzog et al., Suppression and Contrasuppression in Athymic Nude Mice: Nude Mice Produce the Antigen Specific Component of a T Suppressor Factor that Inhibits the Late 24–hr Phase of DTH, but Do Not Generate Suppression nor Contrasuppression of the Early Initiating Phase of DTH; Cell Immunology 127, 130–145 (1990).
Chen et al., Transplantation Tolerance: Evidence for Lyt+, 2–, Qa 1.2+ Suppressor–Inducer T Cells in Allogeneic Thymus–Grafted Nude Mice; Cell Immunology 77, 318 (1983).
Miller et al., An Immunological Suppressor Cell Inactivating Cytotoxic T–Lymphocyte Precursor Cells Recognizing It, Nature 287, 544 (1980).
Simpson et al., Mice with the xid Mutation Lack the Regulatory Antibodies that are Necessary for the Induction of Contrasuppression, Cell Immunology 164, 126 (1995).

Rosenkrantz et al., Both Ongoing Suppression and Clonal Elimination Contribute to Graft–Host Tolerance After Transplantation of HLA Mismatched T Cell–Depleted Marrow for Severe Combined Immunodeficiency; Journal of Immunology 144, 1721 (1990).
Asseman et al., Interleukin 10 is a Growth Factor for a Population of Regulatory T Cells; Gut 42, 157 (1998).
Gebel, et al., Characterization of Circulating Suppressor T Lymphocytes in Bone Marrow Transplant Recipients; Transplantation 43, 258 (1987).
Kunicaka, et al., Induction of Suppressor Cells to T–and B–Cell Proliferative Responses and Immunoglobulin Production by Monoclonal Antibodies Recognizing the CD3 T–Cell Differentiation Antigen, Cellular Immunology 116, 195 (1988).
Knulst, et al., Prevention of Lethal Graft–Versus–Host Disease in Mice by Monoclonal Antibodies Directed Against T Cells or Their Subsets. II. Evidence for the Induction of a State of Tolerance Based on Suppression; Bone Marrow Transplantation 13, 293 (1994).
Gianello, et al., Tolerance to Class I–Disparate Renal Allografts in Miniature Swine; Transplantation 59, 772 (1995).
Deeg, et al., Specific Tolerance and Immunocompetence in Haploidentical, but not in Completely Allogeneic, Canine Chimeras Treated with Methotrexate and Cyclosporine; Transplantation 44, 621 (1987).
Shen, et al., Suppressor Cells and Intrathymic Inoculation of Donor Alloantigens in Cardiac Transplantation; Society of Thoracic Surgeons, 1683 (1995).
Shimomura et al., Tolerance Induction to Cardiac Allografts by Simultaneous or Sequential Intrathymic Inoculation of Disparate Alloantigens; Transplantation 60, 806 (1995).
Rieger et al., Induction of Suppressor Cell Mechanism in Antilymphocyte Serum–Induced Skin Allograft Tolerance in Mice; Folia Biology 25 (Praha), 220 (1979).
Sanada et al., Establishment of Chimerism in Donor Liver with Recipient–Type Bone Marrow Cells Prior to Liver Transplantation Produces Marked Suppression of Allograft Rejection in Rats; Transplantation Int 11, S174 (1998).

(List continued on next page.)

*Primary Examiner*—Deborah Crouch
*Assistant Examiner*—Anne Marie S. Beckerleg
*Attorney, Agent, or Firm*—Banner & Witcoff, Ltd.

[57] ABSTRACT

This invention provides a method for developing immune tolerance in xenogeneic organ graft recipients, in which lympho-hematopoietic cells from an intended organ graft recipient are differentiated within a xenogeneic surrogate, such as a fetal animal. After birth of the surrogate, the matured lympho-hematopoietic cells containing antigen specific regulatory cells, including suppressor cells, veto cells, select B cells, anti-idiotype antibodies, and other related factors responsible for antigen specific tolerance in a surrogate animal are reintroduced into the intended organ graft recipient, in conjunction with an organ transplant or a tissue transplant from the xenograft surrogate. The invention also provides an organ graft repopulated with cells from the intended organ graft recipient produced in a surrogate animal.

55 Claims, 8 Drawing Sheets

OTHER PUBLICATIONS

Qian, et al., Intrathymic Tolerance and Age; Transplantation Proceedings 27, 3391, (1995).

Database Medline, Abstract 82224968 and Transplantation 33(5):510–514 (May 1982).

Proceedings of "Xenograft 25," M. A. Hardy (ed.), Elsevier, 1989.

Alexandre, et al., "Present Experiences in a Series of 26 ABO–Incompatible Living Donor Renal Allografts," Transplantation Proceedings, 19:4538–4532 (1987).

Auchincloss, Hugh, Jr., "Xenogeneic Transplantation," Transplantation, 46:1–20 (1988).

Drugan, et al., "Fetal Organ and Xenograft Transplantation," Am. J. Obstet. Gynecol., 160:289–293 (1989).

Platt, et al., "Discordant Xenografting: Challenges and Controversies," Current Opinion in Immunology, 3:735–739 (1991).

Crombleholme, et al., "Transplantation of Fetal Cells," Am. J. Obstet. Gynecol., 164:218–230 (1991).

Zanjani, et al., "Hematopoietic Chimerism in Sheep and Nonhuman Primates by in Utero Transplantation of Fetal Hematopoietic Stem Cells," Blood Cells, 17:349–363 (1991).

Duncan, et al., "Immunologic Evaluation of Hematopoietic Chimeric Rhesus Monkeys," Transplantation Proceedings, 23:841–843 (1991).

Flake, et al., "In Utero Stem Cell Transplantation," Exp. Hematol., 19:1061–1064 (1991).

Ildstad, et al., "Cross–species Transplantation Tolerance: Rat Bone Marrow–derived Cells Can Contribute to the Ligand for Negative Selection of Mouse T Cell Receptor Vβ in Chimeras Tolerant to Xenogeneic Antigens (Mouse + Rat → Mouse)," J. Exp. Med., 175:147–155 (1992).

Zeng, et al., "Long–Term Survival of Donor–Specific Pancreatic Islet Xenografts in Fully Xenogeneic Chimeras (WF Rat → B10 Mouse)," Transplantation, 53:277–283 (1992).

Srour, et al, "Sustained Human Hematopoiesis in Sheep Transplanted In Utero During Early Gestation With Fractionated Adult Human Bone Marrow Cells," Blood, 79:1404–1412 (1992).

Ezzell, C., "Sheep Chimera Makes Human Blood Cells," Science News, 141:182 (1992).

Zanjani, et al., "Engraftment and Long–Term Expression of Human Fetal Hemopoietic Stem Cells in Sheep Following Transplantation in Utero," The Journal of Clinical Investigation, Inc., 89:1178–1188 (1992).

Groth, et al., "Evidence of Xenograft Function in a Diabetic Patient Grafted With Porcine Fetal Pancreas," Transplantation Proceedings, 24:972–973 (1992).

McCune, et al., "The SCID–hu Mouse: Murine Model for the Analysis of Human Hematolymphoid Differentiation and Function," Science, 241:1632–1639 (1988).

McCune, et al., "The SCID–hu Mouse: Current Status and Potential Applications," Current Topics in Microbiology and Immunology, 152:183–193 (1989).

Mosier, Donald E., "Immunodeficient Mice Xenografted With Human Lymphoid Cells: New Models for In Vivo Studies of Human Immunobiology and Infectious Diseases," Journal of Clinical Immunology, 10:185–191 (1990).

Namikawa, et al., "Long–Term Human Hematopoiesis in the SCID–hu Mouse," J. Exp. Med., 172:1055–1063 (1990).

Kaneshima, et al., "Today's SCID–hu Mouse," Nature, 348:561–562 (1990).

McCune, Joseph M., "SCID Mice as Immune System Models," Current Opinion in Immunology, 3:224–228 (1991).

Mosier, Donald E., "Adoptive Transfer of Human Lymphoid Cells to Severely Immunodeficient Mice: Models for Normal Human Function, Autoimmunity, Lymphomagenesis, and AIDS," Advances Immunology, 50:303–325 (1991).

Tscherning, et al., "$CD3^+$ T Cells in Severe Combined Immunodeficiency (SCID) Mice. V. Allogeneic T Cells Engrafted into SCID Mice Do Not Induce Graft–Versus–Host Disease in Spite of the Absence of Host Veto and Natural Suppressor Cell Activity" Scand. J. Immunol., 34:795–801 (1991).

Krowka, et al., "Human T Cells in the SCID–hu Mouse are Phenotypically Normal and Functionally Component," The Journal of Immunology, 146:3751–3756 (1991).

Vandekerckhove, et al., "Clonal Analysis of the Peripheral T Cell Compartment of the SCID–hu Mouse," The Journal of Immunology, 146:4173–4179 (1991).

Peault, et al., "Lymphoid Reconstitution of the Human Fetal Thymus in SCID Mice with $CD34^+$ Precursor Cells," J. Exp. Med., 174:1283–1286 (1991).

McCune, Joseph M., "The SCID–hu Mouse: A Small Animal Model for the Analysis of Human Hematolymphoid Differentiation and Function," Bone Marrow Transplantation, 9 (Supp. 1):74–76 (1992).

Roncarolo, et al., "SCID–hu Mice as a Model to Study Tolerance after Fetal Stem Cell Transplantation," Bone Marrow Transplantation, 9 (Supp. 1):83–84 (1992).

Huppes, et al., "Acute Human vs. Mouse Graft vs. Host Disease in Normal and Immunodeficient Mice," Eur. J. Immunol., 22:197–206 (1992).

Tary–Lehmann, et al., "Human Mature T Cells That are Anergic In Vivo Prevail in SCID Mice Reconstituted with Human Peripheral Blood," J. Exp. Med., 175:503–516 (1992).

Vandekerckhove, et al., "Human Hematopoietic Cells and Thymic Epithelial Cells Induce Tolerance via Different Mechanisms in the SCID–hu Mouse Thymus," J. Exp. Med., 175:1033–1043 (1992).

Owen, Ray D., "Immunogenetic Consequences of Vascular Anastomoses Between Bovine Twins," Science, 102:400–401 (1945).

Billingham, et al., "'Actively Acquired Tolerance' Of Foreign Cells," Nature, 172:603–606 (1953).

Simonsen, M., "Artificial Production of Immunological Tolerance," Nature, Apr. 30, 1955, pp. 763–764.

Tutschka, et al., "Suppressor Cells in Transplantation Tolerance—II. Maturation of Suppressor Cells in the Bone Marrow Chimera," Transplantation, 32:321–325 (1981).

Tutschka, et al., "Suppressor Cells in Transplantation Tolerance—III. The Role of Antigen in the Maintenance of Transplantation Tolerance," Transplantation, 33:510–514 (1982).

Yoshizawa, et al., "Mouse T Lymphocytes Proliferative Responses Specific For Human MHC Products In Mouse Anti–Human Xenogeneic MLR," The Journal of Immunology, 132:2820–2829 (1984).

Ildstad, et al., "In Vivo and In Vitro Characterization of Specific Hyporeactivity to Skin Xenografts in Mixed Xenogeneically Reconstituted Mice (B10 + F344 Rat → B10)," J. Exp. Med., 160:1820–1835 (1984).

Hamano, et al., "The Effect of Intrathymic Injection of Donor Blood on the Graft Versus Host Reaction and Cardiac Allograft Survival in the Rat," Immunol. and Cell Biol., 69:185–189 (1991).

Wren, et al., "Successful Transfer of Donor–Specific Transplantation Tolerance by Adoptive Transfer of Fully Allogeneic Chimeric Bone Marrow," Transplantation Proceedings, 23:735–736 (1991).

Streilein, J. Wayne, "Neonatal Tolerance of H–2 Alloantigens," Transplantation, 52:1–10 (1991).

Dorf, et al., "Suppressor T Cells: Some Answers but More Questions," Immunology Today, 13:241–243 (1992).

Kroemer, et al., "Mechanisms of Self Tolerance," Immunol. Today, 13:401–404 (1992).

Burdick, James F., "Suppressor Cell Regulation and Allograft Potentiation," in Kidney Transplant Rejection Diagnosis and Treatment, 2nd Ed., J.F. Burdick, L.C. Racusen, K. Solez, G.M. Williams, eds., 1992, pp. 261–317.

Smith, et al., "Successful Induction of Long–Term Specific Tolerance to Fully Allogeneic Renal Allografts in Miniature Swine," Transplantation, 53:438–444 (1992).

Hersh, Evan M., "Blastogenic Responses of Human Lymphocytes to Xenogeneic Cells in Vitro," Transplantation, 12:287–293 (1971).

Moller, et al., "Specificity of Lymphocyte–Mediated Cytotoxicity Induced by In Vitro Antibody–Coated Target Cells," Cellular Immunology, 4:1–19 (1972).

Widmer, et al., "Allogeneic and Xenogeneic Response in Mixed Leukocyte Cultures," J. Exp. Med., 135:1204–1208 (1972).

Sachs, et al., "Transplantation in Miniature Swine," Transplantation, 22:559–567 (1976).

Woolnough, et al., "Cytotoxic and Proliferative Lymphocyte Responses to Allogeneic and Xenogeneic Antigens In Vitro," AJEBAK, 57 (Pt. 5):467–477 (1979).

Swain, et al., "Xenogeneic Human Anti–Mouse T Cell Responses Are Due to the Activity of the Same Functional T Cell Subsets Responsible for Allospecific and Major Histocompatibility Complex–Restricted Responses," J. Exp. Med., 157:720–729 (1983).

Beschorner, et al., "Localization of Hematopoietic Progenitor Cells in Tissue With the Anti–My–10 Monoclonal Antibody," Am. J. Pathol., 119:1–4 (1985).

Loveland, et al., "The non–MHC Transplantation Antigens: Neither Weak Nor Minor," Immunology Today, 7:223–229 (1986).

Marche, et al., "A Variable Region Gene Subfamily Encoding T Cell Receptor β–Chains Is Selectively Conserved Among Mammals," The Journal of Immunology, 137:1729–1734 (1986).

Fink, et al., "Veto Cells," Ann. Rev. Immunol., 6:115–137 (1988).

Speiser, et al., "Positive and Negative Selection of T Cell Receptor $V_\beta$ Domains Controlled by Distinct Cell Populations in the Thymus," J. Exp. Med., 170:2165–2170 (1989).

Ljunggren, et al., "In Search of the 'Missing Self': MHC Molecules and NK Cell Recognition," Immunology Today, 11:237–243 (1990).

Gustafsson, et al., "Class II Genes of Miniature Swine," The Journal of Immunology, 145:1946–1951 (1990).

Tavassoli, et al., "Enhancement of the Grafting Efficiency of Transplanted Marrow Cells by Preincubation With Interleukin–3 and Granulocyte–Macrophage Colony–Stimulating Factor," Blood, 77:1599–1606 (1991).

Torimoto, et al., "CD31, A Novel Cell Surface Marker for CD4 Cells of Suppressor Lineage, Unaltered by State of Activation," The Journal of Immunology, 148:388–396 (1992).

Fields, et al., "Organ Injury Associated with Extrathymic Induction of Immune Tolerance in Doubly Transgenic Mice," Proc. Natl. Acad. Sci., USA, 89:5730–5734 (1992).

Cros, et al., "Oligonucleotide Genotyping of HLA Polymorphism on Microtitre Plates," The Lancet, 340:870–873 (1992).

LeGuern, et al., "Expression of Swine Class II Genes Using Recombinant Retroviral Vectors," Transplantation Proceedings, 23:427–428 (1991).

Shafer, et al., "Expression of a Swine Class II Gene in Murine Bone Marrow Hematopoietic Cells by Retroviral–Mediated Gene Transfer," Proc. Natl. Acad. Sci., USA, 88:9760–9764 (1991).

Emery, et al., "Expression of Allogeneic Class II cDNA in Swine Bone Marrow Cells Transduced With a Recombinant Retrovirus," Transplantation Proceedings, 24:468–469 (1992).

Sykes, et al., "Specific Prolongation of Skin Graft Survival Following Retroviral Transduction of Bone Marrow with an Allogeneic Major Histocompatibility Complex Gene," Transplantation, 55:197–202 (1993).

Bishop, Jerry E., "DNX, Duke Take First Step in Altering Pigs to Make Organs Transplantable," The Wall Street Journal, Sep. 29, 1993.

Williams, et al., "Host Repopulation of the Endothelium in Allografts of Kidneys and Aorta," in Surgical Forum, 20:293–294 (1969).

Williams, et al., "Host Repopulation of Endothelium," Transplantation Proceedings, 3:869–872 (1971).

Parks, et al., "Biological Significance of Endothelial Repopulation in Allografted Vessels," in Surgical Forum, 23:290–291 (1972).

Gale, et al., "Bone Marrow Origin of Hepatic Macrophages (Kupffer Cells) in Humans," Science, 201:937–938 (1978).

Starzl, et al., "Systemic Chimerism in Human Female Recipients of Male Livers," The Lancet, 340:876–877 (1992).

Skowron–Cendrzak, et al., "Suppression of Local Graft–Versus–Host Reactions by Mouse Fetal & Newborn Spleen Cells," Eur. J. Immunol., 6:451–452 (1976).

Michel, et al., "Study of the Local Graft Versus Host Reaction in the Rat," Journal of Surgical Research, 41:347–351 (1986).

Shaffer, et al., "Studies in Small Bowel Transplantation," Transplantation, 45:262–69 (1988).

Shaffer, et al., "Prevention of Graft–Versus–Host Disease Following Small Bowel Transplantation With Polyclonal and Monoclonal Antilymphocyte Serum," Transplantation, 52:948–52 (1991).

Terasaki, et al., "Destruction of Lymphocytes In Vitro By Normal Serum From Common Laboratory Animals," J. Immun., 87:383–395 (1961).

Snyder, et al., "Prolongation of Renal Xenografts by Complement Suppression," Surgical Forum, 17:478–480 (1966).

McKenzie, et al., "Human Lymphocytotoxic and Hemagglutinating Activity Against Sheep and Pig Cells," The Lancet, Aug. 17, 1968, pp. 386–387.

Fearon, D.T., "Anti–Inflammatory and Immunosuppressive Effects of Recombinant Soluble Complement Receptors," Clin. Exp. Immunol., 86:43–46 (1991).

Xia, et al., "Prolongation of Guinea Pig Cardiac Xenograft Survival in Rats by Soluble Human Complement Receptor Type 1," Transplantation Proceedings, 24:479–480 (1992).

Todo, et al., "Immunosuppression of Canine, Monkey, and Baboon Allografts by FK 506: With Special Reference to Synergism with Other Drugs and to Tolerance Induction," Surgery, 104:239–249 (1988).

Morris, Randall E., "Rapamycin: FK506's Fraternal Twin or Distant Cousin?," Immunology Today, 12:137–140 (1991).

Schreiber, et al., "The Mechanism of Action of Cyclosporin A and FK506," Immunol. Today (England), 13:136–142 (1992).

Evans, et al., "Fetal Surgery in the 1990s," AJDC, 143:1431–1436 (1989).

Harrison, Michael R., "Fetal Surgery," West J. Med., 153:648 (1990).

Longaker, et al., "Update on the Status of Fetal Surgery," Surg. Annual., 23:53–68 (1991).

Harrison, et al., "The Fetus As A Patient," Ann. Surg., 213:279–289 ((1991).

Mosier, et al., Nature, 335:256–259 (1988).

Hammer, et al., "Suppressor Cell Activity in Human Renal Allograft Recipients," Proc EDTA, 18:454–458 (1981).

Wramner, et al., "Evidence of Donor–Specific Cellular Suppressor Activity in Donor–Specific Cell Mediated Lympholysis Unresponsiveness in Renal Transplant Patients," Transplantation, 44(3):390–395 (1986).

Gruner, et al., "Inhibition of Langerhans Cell ATPase and Contact Sensitization by Lanthanides—Role of T–Suppressor Cells," Journal of Investigative Dermatology, 97(3):478–482 (1991).

Turka, et al., "In Vivo Activity of Mixed Lymphocyte Response–Generated Suppressor Cells and Ability to Prolong Cardiac Allograft Survival in Rats," Transplantation, 47(2):388–390 (1989).

Tscherning et al. (1991) Scand. J. Immunol., vol. 34, 795–801 cited by applicant in text, p. 11–12.

Zheng et al. (1992) Transplantation, vol. 53, 277–283 cited by applicant in text, p. 11–12.

Posselt et al. (1990) Science, vol. 249, 1293–1296 cited by applicant in text, p. 11–12.

Jacobsen et al. (1998) APMIS, vol. 106, 345–353.

Rachimim et al. (1998) Transplantation, vol. 65, 1386–1393.

Webster's Collegiate Dictionary, 10th ed., 1996.

R.P. Lanza et al. Sci. Amer. (Jun. 1997) pp. 54–59.

J. P. Ridge et al. Science 271:1723–6 '96.

T. M. Crombleholme J. Ped. Surg. 25(8) :885–92 '90.

J. Manhalouis et al. Developmental & Comparative Immunol. 17:41–53, '93.

D. Higgins et al Dev. & Comp. Immunol. 17: 341–355, '93.

A. Abbas et al., Cellular & Molecular Immunology, W. B. Saunders Co., Philadelphia, 1991, pp. 22, 23, 205–207, '91.

R. Soiffer et al. Blood 82(7) 2216–23 Abstract, '93.

J. Davies et al. J. Immunology 157(2) 529–33 Abstract, '96.

R. Click et al. Transplantation (Baltimore) 58(9): 1020–6, '94.

A. Van den Eertwegh Crit. Rev. in Immunology 11(6) 337–80, '92.

C. Martin et al. (Abstract) Develop. Immunol. ('91) 1(4):265–77.

R. Kast Medical Hypotheses 4:173–77 ('78).

L. Rayfield et al. Transplant. 36(2):183–9 ('83).

K. Hamano et al. Immunol. & Cell Biol. 691 185–9 ('91).

P. McCullagh Immunol. 67:489–95 ('89).

P. McCullagh Transplant. 46(2):280–5 ('88).

D. Cranston et al. Transplant. 43(6) 809–813 ('87).

SURROGATE TOLEROGENESIS FOR THE DEVELOPMENT OF TOLERANCE TO XENOGRAFTS

This application is a continuation of U.S. Ser. No. 08/065,370 filed May 24, 1993.

BACKGROUND OF THE INVENTION

1. Field of the Invention

The field of the present invention relates to the transplanting of organs and tissues, and more particularly to the production in a surrogate of regulatory cells and factors capable of generating immune tolerance to a graft organ in the recipient and to subsequently transplanting xenografts from the surrogate to a recipient. The invention also relates to methods for producing within a surrogate, organs for transplant that are repopulated with cells from the organ graft recipient, lessening the antigen difference and therefore the risk of rejection.

2. Review Of The Related Art

The normal immune system is capable of specifically differentiating between "self" and foreign entities, with foreign entities including infectious agents. The ability to differentiate self from foreign entities is established naturally during fetal development, when the developing immune system of the fetus is programmed to recognize presented antigens as self; i.e. as antigens of the fetus. Several mechanisms are responsible for immune tolerance; including suppression, negative selection, and anergy. Suppression refers to the inhibition of lymphocytes that are reactive to self antigens. Negative selection refers to prevention of the development of immune clones capable of reacting with self antigens. Anergy refers to cells that recognize self but fail to proliferate or function in response to the self antigen.

Suppressor and regulatory T cells block the proliferation of self-reactive lymphoid cells, usually through the secretion of soluble factors. Upon recognition by a self-reactive precursor T cell, the self-reactive cells are suppressed. A network of antibodies and T cell receptors may develop the capability to react against the reactive components of self-reactive antibodies and T cells receptors, with the network of antibodies and T cell receptors also known as an anti-idiotype network. The antibodies and T cell receptors then neutralize self-reactive cells. Veto cells are T cells that express a self antigen.

The principal problems associated with organ transplantation are immune rejection and a shortage of acceptable donors. Unless the donor is an identical twin, the immune system of the recipient recognizes the graft as foreign and the recipient's immune system tries to reject the graft. Although immune suppression may postpone rejection for prolonged periods, immune suppression places the recipient at risk for infections and malignancies. Despite requiring chronic immune suppression, most organ and tissue transplants are successful in saving lives and improving the quality of life. The list of successfully transplanted tissues includes: kidney, heart, lung, liver, corneas, pancreas, pancreatic islets of Langerhans, intestines, brain tissue, liver, spleen, thymus, lymph nodes, bone marrow, skin, and bones. Combinations of tissue have also been transplanted; for example, heart-lung transplants, pancreas-kidney transplants, and pancreas-kidney-intestinal transplants.

Because of the relative success of the above organ and tissue transplants, a marked shortage of human organ donors exists. For example, although nearly 9,500 kidney transplants are performed annually in the United States, approximately 40,000 Americans develop end stage renal disease annually, and these 40,000 Americans could benefit from organ transplants. Xenografts, herein defined as transplants from another species, could potentially resolve the shortage of transplantable organs and tissues, but the risk of rejection is considered to be even greater than for allografts, herein defined as transplants from a non-identical donor of the same species.

Because of the severe shortage of human organ donors, transplant recipients have occasionally received a xenograft for short term life support, with the short term xenograft also referred to as a bridge transplant. By using bridge transplants of xenografts, additional time is provided to locate a suitable human donor.

Immune tolerance for new transplant grafts has been induced in graft recipients using bone marrow transplants. The patient's immune system is destroyed with high dose chemotherapy and/or total body irradiation. Autologous marrow is then infused into the patient simultaneous with the patient being exposed to the transplant or corresponding transplant antigens. As the immune system of the patient reconstitutes, the immune system recognizes the transplant antigens as self, along with the patient's own antigens. Although the procedure may be used for children and adults, the procedure exposes the patients to long term immune deficiency while the immune system repopulates and reconstitutes in the patient. Thus the patient is at considerable risk for infections and malignancies. Aggressive chemotherapy and/or irradiation may also be toxic to many of the patient's organs and tissues; for example, the lung, the liver, and the intestines.

The fetal or neonatal period offers a window of opportunity to develop tolerance to new antigens with less danger to the patient. When a fetus or neonate, i.e. newborn, is exposed to foreign antigens, including tissues from another species, the fetus or neonate, after maturation, is later specifically tolerant and capable of accepting grafts from the original source of the foreign antigen without immune suppression. Therefore, human fetuses may be exposed to antigens from a potential donor and receive post-natally a graft from the potential donor.

The donor is not limited to being human; i.e. other species may serve as donors for the human fetus exposed in the above manner. For example, certain congenital heart and hematological diseases may be diagnosed before birth using echocardiography or amniocentesis. A human fetus with a left ventricular syndrome may receive an intrauterine infusion of baboon cells from a specific donor baboon. After birth, the infant would receive a heart by transplant from the specific donor baboon using the above method. The infant, on receiving the transplanted heart, does not require immune suppression. Although the above method represents an elegant application of basic immunology principles, the method fails to address the transplant needs of the vast majority of patients having diseases recognized or diagnosed after birth, long after the prenatal or neonatal window of opportunity closes for the patients.

A variety of methods have been investigated for suppression of graft rejection, including gene therapy; transplants conducted on human fetuses by bone marrow replacement or other methods; and immune suppression by various drugs. Other studies focus on inducing immune tolerance to transplantation for allografts and xenografts by the introduction of foreign tissue in neonatal and post-natal recipients. The art discloses infusing human cells into non-human animals during the earliest stage of development of the non-human animal for incubating and harvesting hTCGF, and the art also discloses inducing transplantation immune tolerance by bone marrow transplantation or fetal stem cells to develop chimeras. Throughout, immune tolerance is induced within the transplant organ recipient.

U.S. Pat. No. 4,624,917 to Suaimoto discloses a process for producing human T-cell growth factor (hTCGF) by infusing human cells capable of producing hTCGF into non-human warm blooded animals, with the animals preferably at an immature stage; i.e. as eggs, embryos, fetuses, or newborn or infant animals. The development of the animal allows the infused human cells to develop and reproduce for later harvesting of the hTCGF.

U.S. Pat. No. 5,004,681 to Boyse et al. teaches obtaining hematopoietic stem cells and progenitor cells from neonatal or fetal blood. The obtained cells are cryogenically preserved for later use in hematopoietic or immune reconstitution and in gene therapy. U.S. Pat. No. 5,061,620 to Tsukamoto et al. teaches a method for isolating human hematopoietic stem cells in substantially homogeneous quantities.

Japanese Abstract No. 126519 teaches cultivating juvenile cells having the same genes and cytoplasm of an aged or sick person using an actual or artificial uterine environment, a normal cell incubator, or a cell propagation promoter. The cultivated juvenile cells are later used in parts of the body of the aged or sick person. Japanese Abstract No. 63-170322 teaches cultivating monogenetic cells for later transplanting to developed cells. Japanese Abstract No. 1-132528 discloses using the immune suppression property of human immunoglobulin GI protein (IgGl) by injection of IgGl into a recipient prior to transplantation. Japanese Abstract No. 63-39820 teaches using immune suppression drugs during transplantation of juvenile cells into an aged recipient.

H. Auchincloss, Jr., "Xenogeneic Transplantation—A Review", TRANSPLANTATION, Vol. 46, No. 1, July 1988, pp. 1–20, discusses the methods implemented for xenogeneic transplantation. In particular, Auchincloss discloses the induction in the recipient of neonatal tolerance for allografts and xenografts by the introduction of donor antigens in the recipient at the neonatal or embryonic stage of life. Auchincloss speculates toward achieving tolerance induction by using the principle of presenting foreign antigens at the time of maturation of T lymphocytes to enable the cells to consider the foreign antigens as self, thereby avoiding the development of the functions or suppressing the functions of the cells responsive to the foreign determinants.

R. E. Billingham et al., "Actively Acquired Tolerance of Foreign Cells", NATURE, Vol. 172, Oct. 3, 1953, pp. 603–606, discusses "actively acquired tolerance" to initiate tolerance by the first presentation of foreign tissue during the fetal phase, with resistance to a later transplanted grafts being abolished or reduced. M. Simonsen, "Artificial production of immunological tolerance. Induced tolerance to heterologous cells and induced susceptibility to virus", NATURE, Vol. 174, Apr. 30, 1955, pp. 763–764, demonstrates neonatal tolerance to xenoantigens (from a different species) by injecting the xenogeneic cells into bird embryos. The subsequent titers of natural antibodies to the donor were significantly reduced.

R. D. Owen, "Immunogenetic consequences of vascular anastomoses between bovine twins", SCIENCE, Vol. 102, 1949, pp. 400–401, suggests that the tolerance between dissimilar bovine littermates is due to exchange of blood during fetal development due to vascular connections within the placenta between the litter mates. J. W. Streilein, "Neonatal tolerance of H-2 alloantigens. Procuring graft acceptance the 'old-fashioned' way", TRANSPLANTATION, Vol. 52, July 1991, pp. 1–10, reviews the mechanisms of neonatal tolerance. Depending on the combination of allogeneic murine strains, this can be due to negative selection, anergy, or suppression.

A. W. Flake et al., "In Utero Stem Cell Transplantation", EXPERIMENTAL HEMATOLOGY, Vol. 19, 1991, pp. 1061–4, discusses future directions for in utero transplantation of hematopoietic stem cells (HSC), including prenatal-specific tolerance induction for post-natal allogeneic and xenogeneic transplantation.

E. D. Zanjani et al., "Engraftment and Long-Term Expression of Human Hemopoietic Stem Cells in Sheep Following Transplantation In Utero", J. CLIN. INVEST., Vol. 89, April 1992, pp. 1178–1188, discusses inducing tolerance in sheep by transplanting hematopoietic stem cells from human fetal donors to sheep fetuses. The authors also teach the use of growth factors such as recombinant human IL-3 and GM-CSF to enhance donor hematopoiesis within the xenogeneic fetus. They suggest that hematopoietic stem cells can be stored and expanded as a "reservoir of human HSC" within the fetus for later use. They suggest that human immunoglobulins may also be produced in utero. E. D Zanjani et al., "Hematopoietic Chimerism in Sheep and Nonhuman Primates by In Utero Transplantation of Fetal Hematopoietic Stem Cells", BLOOD CELLS, Vol. 17, 1991, pp. 349–363, discloses transplanting fetal stem cells to an unrelated fetal animal, resulting in long-term stable hematopoietic chimerism.

E. F. Srour et al., "Sustained Human Hematopoiesis in Sheep Transplanted In Utero during Early Gestation with Fractionated Adult Human Bone Marrow Cells", BLOOD, Vol. 79, No. 6, 1992, pp. 1404–12, teaches the concept of fetuses representing the ideal host for HSC transplantation, and of transplanting human cells enriched for hematopoietic progenitor and stem cells to produce chimera. As with the previous articles (Zanjani et al), the studies are described as a preclinical study for treatment of human fetuses. Human fetuses would receive allogeneic cells in utero. C. Ezzell, "Sheep chimera makes human blood cells", SCIENCE NEWS, Vol. 141, Mar. 21, 1992, p. 182, comments on the Srour study (above) and lists human genetic blood disorders that can be diagnosed in utero and therefore treated by intrauterine infusion of cells.

M. Tavassoli et al., "Enhancement of the Grafting Efficiency of Transplanted Marrow Cells by Preincubation with Interleuidn-3 and Granulocyte-Macrophage Colony-Stimulating Factor", BLOOD, Vol. 77, April 1991, pp. 1599–1606, demonstrates that preincubation of murine bone marrow cells with IL-3 or GM-CSF enhanced subsequent engraftment in irradiated syngeneic hosts. B. W. Duncan et al., "Immunologic Evaluation of Hematopoietic Chimeric Rhesus Monkeys", TRANSPLANT. PROC., Vol. 23, February 1991, pp. 841–3, evaluates T cell maturation and function after fetal rhesus monkey hematopoietic cells from a fetal liver are injected into a mismatched rhesus fetus.

T. M. Crombleholme et al., "Transplantation of Fetal Cells", AM. J. OBSTET. GYNECOL, Vol. 164, January 1991, pp. 218–230, reviews the art for the use of fetal tissue donors and fetal tissue recipients. The review lists multiple human congenital hematologic diseases that could be treated by a marrow infusion when the patient is a fetus. Fetal tissue can also be used for donation, such as pancreatic islet cells for the treatment of diabetes mellitus and dopaminergic neurons for the treatment of Parkinson's disease. The art does not propose alterations of the fetal tissue prior to transplantation. C. G. Groth et al., "Evidence of xenograft function in a diabetic patient grafted with porcine fetal pancreas" TRANSPLANT. PROC., Vol. 24, June 1992, pp. 972–973, transplanted pancreatic islet cells from fetal pigs into a diabetic patient. The islets were not altered prior to transplantation.

The art concerning human-SCID mouse chimeras demonstrates that human lymphocytes can differentiate within a SCID mouse and become tolerant to the mouse. The human-SCD mouse chimera art teaches that tolerance to the mouse is by negative selection and possibly anergy, but not by suppression.

Mosier et al., "Transfer of a Functional Human Immune System to Mice with Severe Combined Immunodeficiency", NATURE, Vol. 335, 1988, pp. 256–259, discusses the expansion and differentiation of human lymphoid cells from peripheral blood within the SCID mouse. D. E. Mosier., "Immunodeficient Mice Xenografted with Human Lymphoid Cells: New Models for In Vivo Studies of Human Immunobiology and Infectious Diseases" J. CLIN. IMMUNOL. Vol. 10, 1990, pp. 185–191, and D. E. Mosier, "Adoptive Transfer of Human Lymphoid Cells to Severely Immunodeficient Mice: Models for Normal Human Immune Function, Autoimmunity, Lymphomagenesis, and AIDS", ADV. OL., Vol. 50, 1991, pp. 303–325 review the potential uses of these models such as the study of AIDS, the immune reactions to infectious diseases, and effect of drugs on the human immune system.

J. M. McCune et al., "The SCID-hu Mouse: Murine Model for the Analysis of Human Hematolymphoid Differentiation and Function", SCIENCE, Vol. 241, 1988, pp. 1632–1639, teaches the implantation of human fetal thymus, lymph node, or fetal liver hematopoietic stem cells in the SCID mouse and the differentiation of human lymphocytes and immunoglobulins. R. Namikawa et al., "Long-Term Human Hematopoiesis in the SCID-hu Mouse", J. EXP. MED., Vol. 172, October 1990, pp. 1055–1063, discloses co-implantation of human fetal thymus and liver in the SCID mouse leading to long term survival of human hematopoietic and lymphoid cells without the development of graft-vs-host disease.

B. Peault et al., "Lymphoid Reconstitution of the Human Fetal Thymus in SCID Mice with CD34+ Precursor Cells", J. EXP. MED., Vol. 174, November 1991, pp. 1283–1286, teaches that infusion of human hematopoietic stem cells leads to repopulation of human thymus fragments in the SCID mouse with human cells. J. F. Krowka et al., "Human T Cells in the SCID-hu Mouse are Phenotypically Normal and Functionally Competent", J. IMMUNOL., Vol. 146, June 1991, pp. 3751–3756, teaches that immature human cells mature into populations of mature T cells within SCID mice receiving fetal implants of human thymus and liver. B. A. E. Vandekerckhove et al., "Clonal Analysis of the Peripheral T Cell Compartment of the SCID-hu Mouse", J. IMMUNOL., Vol. 146, June 1991, pp. 4173–4179, teaches the maturation of human lymphocytes from fetal thymus and liver fragments into mature T cells with polyclonal and alloreactive T cell receptors, but without self-reactive T cell receptors.

H. Kaneshima et al., "Today's SCID-hu Mouse", NATURE, Vol. 348, December 1990, pp. 561–562, J. M. McCune et al., "The SCID-hu Mouse: Current Status and Potential Applications", CURRENT TOPICS IN MICROBIOLOGY AND IMMUNOLOGY, Vol. 152, 1989, pp. 183–193, J. M. McCune, "SCID Mice as Immune System Models", CURRENT OPINION IN IMMUNOLOGY, Vol 3, 1991, pp. 224–229, and J. M. McCune, "The SCID-hu Mouse: a Small Animal Model for the Analysis of Human Hematolymphoid Differentiation and Function", BONE MARROW TRANSPLANTATION, Vol 9 (Suppl 1), 1992, pp. 74–76, review the SCID-hu model and possible applications in the study of human immunobiology, such as the study of AIDS and anti-HIV drugs, hematopoiesis, and immune reactions.

W. Huppes et al., "Acute Human vs. Mouse Graft-vs.-Host Disease in Normal and Immunodeficient Mice", EUR. J. IMMUNOL., Vol. 22, 1992, pp. 197–206, teaches that human peripheral lymphocytes can survive in mice that are artificially immunosuppressed or hereditarily immunodeficient such as the SCID mouse, providing natural antibodies are removed. Engraftment with large numbers of human lymphocytes, however, was associated with severe graft-vs-host disease (human vs. mouse).

M. Tary-Lehmann and A. Saxon, "Human Mature T cells that are Anergic In vivo Prevail in SCID Mice Reconstituted with Human Peripheral Blood", J. EXP. MED., Vol. 175, February 1992, pp. 503–516, teach that human cells mature into memory T cells with alpha/beta T cell receptors, but that the cells are anergic and fail to be stimulated by anti-CD3 antibodies. The anergy was reversible. T. Tscheming et al., "CD3+ T Cells in Severe Combined Immunodeficiency (SCID) mice. V. Allogeneic T Cells Engrafted into SCID Mice do not Induce Graft-versus-Host Disease in Spite of the Absence of Host Veto and Natural Suppressor Cell Activity", SCAND. J. IMMUNOL., Vol. 34, 1991, pp. 795–801, teaches that the tolerance of allogeneic murine lymphocytes engrafted within SCID mouse to the SCID mouse is not due to host veto cells or to natural suppressor cells. M-G. Roncarolo and B. Vandekerckhove, "SCID-hu Mice as a Model to Study Tolerance after Fetal Stem Cell Transplantation", "BONE MARROW TRANSPLANTATION", Vol. 9 (Suppl 1), February 1992, pp. 83–84, and B. A. E. Vandekerckhove et al., "Human Hematopoietic Cells and Thymic Epithelial Cells induce Tolerance via Different Mechanisms in the SCID-hu Mouse Thymus", J. EXP. MED., Vol. 175, April 1992, pp. 1033–1043, produce SCID-hu chimeras using a fetal thymus from one donor and fetal liver hematopoietic cells from another donor. The lymphocytes derived from the two human donors are tolerant to each other. Tolerance to the liver donor was by negative selection whereas tolerance to the thymus donor did not involve negative selection, but presumably by anergy. Most notably, mixing studies indicate that the immune tolerance was not due to suppression.

Y. J. Zeng et al., "Long-term Survival of Donor-Specific Pancreatic Islet Xenografts in Fully Xenogeneic Chimeras (WF Rat→B10 Mouse)", TRANSPLANTATION, Vol. 53, February 1992, pp. 277–283, teaches that mice treated with lethal irradiation and rat marrow cells were later tolerant to and accepted pancreatic islet cells from rats. S. T. Ildstad et al., "Cross-Species Transplantation Tolerance: Rat Bone Marrow-Derived Cells can Contribute to the Ligand for Negative Selection of Mouse T Cell Receptor V Beta in Chimeras Tolerant to Xenogeneic Antigens (Mouse+Rat→Mouse)", J. EXP. MED., Vol. 175, January 1992, pp. 147–155, discloses that when mice are lethally irradiated and transplanted with a mixture of rat and murine marrow cells, the chimera is tolerant to the corresponding rat and murine histocompatibility antigens. The tolerance is due to negative selection. A. M. Posselt et al., "Induction of Donor-Specific Unresponsiveness by Intrathymic Islet Transplantation", SCIENCE, 1991, pp. 1293–6, demonstrates the development of tolerance to pancreatic islets in allogeneic rats by injection of donor islets into the thymus after treatment with antilymphocyte serum. Tolerance is demonstrated to be due to negative selection rather than suppression.

K. Hamano et al., "The Effect of Intrathymic Injection of Donor Blood on the Graft versus Host Reaction and Cardiac Allograft Survival in the Rat", IMMUNOLOGY AND CELL BIOLOGY, Vol. 69, 1991, pp. 185–189, demonstrated a decreased graft-vs-host reaction when the donor of the hematopoietic and lymphoid cells received a previous intrathymic injection of host strain cells. Since the donor provided all of the immunoreactive cells and the host provided the target organs, this experiment is equivalent to injecting organ donor cells into the thymus of an organ recipient. Indeed, it was described as a model for heart graft rejection after injection of heart donor cells into the thymus of the heart graft recipient. Because the immune reactive cells of the host were killed by lethal irradiation, the mechanism of tolerance in the lymphocyte donor is irrelevant. Tolerance due only to negative selection or anergy could be transferred to the host as well as suppressor cells.

G. M. Williams et al., "Host Repopulation of Endothelium", TRANSPLANT. PROC., Vol. 3, March 1971, pp. 869–72 discloses that the endothelial cells of aorta grafts are replaced in 2 to 4 months by recipient endothelial cells. In bone marrow chimeras, there was partial repopulation of the endothelial cells in the bone marrow by donor derived cells. R. P. Gale et al., "Bone Marrow Origin of Hepatic Macrophages (Kupffer Cells) in Humans", SCIENCE, Vol. 201, September 1978, pp. 937–938, teaches that the Kupffer cells in the liver of allogeneic marrow recipients are replaced with donor cells.

The art demonstrates that transplant organ grafts can be partially repopulated with recipient cells within the organ graft recipient and that the marrow vascular endothelium in bone marrow recipients partially repopulate with donor cells.

D. Shafer et al., "Studies in Small Bowel Transplantation. Prevention of Graft-versus-Host Disease with Preservation of Allograft Function by Donor Pretreatment with Antilymphocyte Serum", TRANSPLANTATION, Vol. 45, February 1988, pp. 262–269, and D. Shafer et al., "Prevention of Graft-versus-host Disease Following Small Bowel Transplantation with Polyclonal and Monoclonal Antilymphocyte Serum", TRANSPLANTATION, Vol. 52, teaches that GvHD by lymphocytes from the intestine is a major problem after intestinal transplants. They disclose that GvHD can be prevented by treating the donor with antilymphocyte serum (ALS, either polyclonal or monoclonal) at the time of or before transplantation. The effectiveness correlates with the depletion of lymphocytes in the attached mesenteric lymph nodes. The graft is not repopulated ex vivo with organ graft recipient cells. Nor does the treatment with ALS remove the cellular targets of rejection, including endothelium, macrophages, dendritic cells, plasma cells, etc. Although the risk of GvHD from the intestinal transplant is reduced, the graft is still at risk for rejection and is still immune deficient and at risk for infections. The authors note that "its use in clinical transplantation may be limited by time or logistical constraints . . . "

G. E. Shafer et al., "Expression of a Swine Class II Gene in Murine Bone Marrow Hematopoietic Cells by Retroviral-Mediated Gene Transfer", Proc. Natl. Acad. Sci. USA, Vol. 88, November 1991, pp. 9760–9764, and D. W. Emery et al., "Expression of Allogeneic Class II cDNA in Swine Bone Marrow Cells Transduced with a Recombinant Retrovirus", TRANSPLANT. PROC., Vol. 24, April 1992, pp. 468–469, suggests that allogeneic and xenogeneic tolerance can be achieved by transgenic engineering and insert the genetic code for swine class II MHC antigens into murine myelopoietic precursor cells and into allogeneic swine cells. Tolerance to the organ donor would be induced in the organ recipient by inserting the donor MHC antigen genes into the recipient hematopoietic stem cells and performing an autologous bone marrow transplant on the recipient using the altered stem cells. The authors do not propose that the genetically altered cells replace the organ donor cells in the graft organ.

The relevant art also does not disclose a protocol for inducing transplantation immune tolerance in the organ donor animals prior to transplantation of grafts from the donor animals to the organ graft recipient. Nor does the prior art suggest the production and expansion of antigen specific suppressor cells, veto cells, cells producing anti-idiotype antibodies or anti-idiotypic antibodies responsible for immune tolerance within the organ graft donor for harvest and transfer back to the organ graft recipient.

OBJECTS OF THE INVENTION

An object of the invention is to provide a source of antigen-specific regulatory cells and factors, including suppressor cells, veto cells, antigen presenting cells defective for B7 and related surface molecules, cells producing anti-idiotype antibodies and anti-idiotypic antibodies for the purpose of inducing immune tolerance in an organ transplant recipient to the antigen.

Another object of the invention is a method for generating regulatory cells including suppressor cells, veto cells, antigen presenting cells defective for B7 and related surface molecules, cells producing anti-idiotype antibodies and anti-idiotypic antibodies responsible for immune tolerance to an organ donor using the surrogate as a third party.

An additional object of the invention is the production of organ xenografts repopulated with organ recipient cells, including but not limited to endothelial cells, dendritic cells, macrophages, lymphocytes, and plasma cells. Another object is a method for the production of organ xenografts repopulated with organ recipient cells in a surrogate, using a fetal animal or a recipient of a bone marrow transplant as a surrogate.

These and other objects are achieved by one or more of the following embodiments of this invention.

SUMMARY OF THE INVENTION

The present invention provides, in one embodiment, a method of transplanting an organ from a donor animal to a recipient animal which is not syngeneic with the donor animal, comprising administering to said recipient animal a cell population containing immunosuppressor moieties in an amount sufficient to reduce specific immune response of the recipient animal to tissue of the donor animal, wherein the cell population is obtained from a surrogate animal which is a chimeric animal containing lymphocytes derived from the recipient animal, and subsequently transplanting an organ from the donor animal to the recipient animal, whereby the immune response of the recipient animal to the organ is reduced.

In another embodiment, the invention provides a method for xenograft transplant of an organ to a recipient animal from a donor animal, wherein the recipient is made immunotolerant to donor tissue, by collecting a first cell population from the recipient, the first cell population containing lymphocytic progenitor cells, but a reduced number of cells that are specifically cytotoxic to tissue from a surrogate animal, administering the first cell population to the surrogate, when the surrogate is in a state of immune deficiency, developing the surrogate into a state of immune competence, collecting from the immune competent surrogate a second population of cells, the second cell population containing immune regulatory moieties which specifically suppress the immune response of the recipient to tissue of the surrogate, infusing the second population of cells into the recipient excising an organ from a donor animal which is antigenically identical to the surrogate, and transplanting the excised organ into said the xenograft recipient.

In yet another embodiment, the invention provides a kit for suppression of immune rejection by a recipient animal of an organ transplanted from a donor animal, comprising an immune suppressive composition containing a cell population obtained from a surrogate animal which is a chimeric animal containing lymphocytes derived from the recipient animal, the cell population containing immunosuppressor moieties specifically suppressing immune response of the recipient animal to tissue of the donor animal, wherein the cell population is suspended in a medium suitable for injection into the recipient animal.

In still another embodiment, the present invention provides a kit for organ transplant into a recipient animal comprising a bodily organ excised from a species different from the recipient animal and perfusion solution in an amount sufficient to preserve the excised organ in condition suitable for transplant into the recipient animal, wherein the organ contains at least a plurality of resident cells selected from endothelial cells, monocytes, dendritic cells, and epithelial cells, which are cells from the same species as the recipient.

The present invention, as embodied and broadly described herein, develops immune tolerance to xenografts, in part, by differentiating lympho-hematopoietic cells from an intended xenograft organ recipient in a xenograft surrogate animal. The intended xenograft recipient is typically a human patient in need of an organ graft. The xenograft surrogate animal preferably is a fetal mammal of another species. "Human" or "organ graft recipient" regulatory cells and factors may be produced and expanded in a chimeric animal to provide antigen specific immune tolerance to an organ graft recipient. The matured lymphocytes and factors are harvested from the surrogate and reinfused into the intended xenograft recipient in conjunction with an organ transplant or a tissue transplant from the xenograft surrogate animal. Instead of inducing tolerant regulatory cells and factors in the organ graft recipient, the human regulatory cells and factors are produced in surrogate animals outside of the intended organ graft recipient.

In a preferred embodiment, multiple surrogate animals are infused with lympho-hematopoietic cells from the intended organ graft recipient. The best surrogate is selected on the basis of the degree of immune tolerance conferred by cells and factors and the best surrogate is then used as a source of tolerant cells and factors and organ graft.

Hematopoietic and lymphoid cells, including lymphocyte progenitors, are obtained from the transplant organ graft recipient, and cultured in a surrogate animal when the surrogate animal is in an initially immune deficient state, such as a fetus. When the surrogate animal fetus is allowed to develop, the cells become immune tolerant to the tissues of the surrogate animal. The cultured lymphocytes and factors are taken from the developed surrogate animal, and infused back into the intended transplant organ graft recipient. The surrogate tissue, for example, an organ, is then taken from the developed surrogate animal, and transplanted into the organ recipient.

Reconstitution of the graft with cells from the organ recipient, including dendritic cells, macrophages, lymphocytes and plasma cells and endothelial cells are described with the modification occurring outside of the intended organ graft recipient.

The invention provides organ grafts that are less susceptible to rejection by repopulating the organ with cells from the intended transplant organ recipient. Acceptance of the surrogate organ graft by the recipient is enhanced by replacement and repopulation of the organ graft by cells from the intended organ graft recipient.

Additional objects and advantages of the invention are set forth in part in the description which follows, and in part are apparent to one skilled in the art from the description. The objects and advantages of the invention also may be realized and attained by means of the instrumentalities and combinations particularly pointed out in the appended claims.

DETAILED DESCRIPTION OF THE PREFERRED EMBODIMENT

Figure 1:
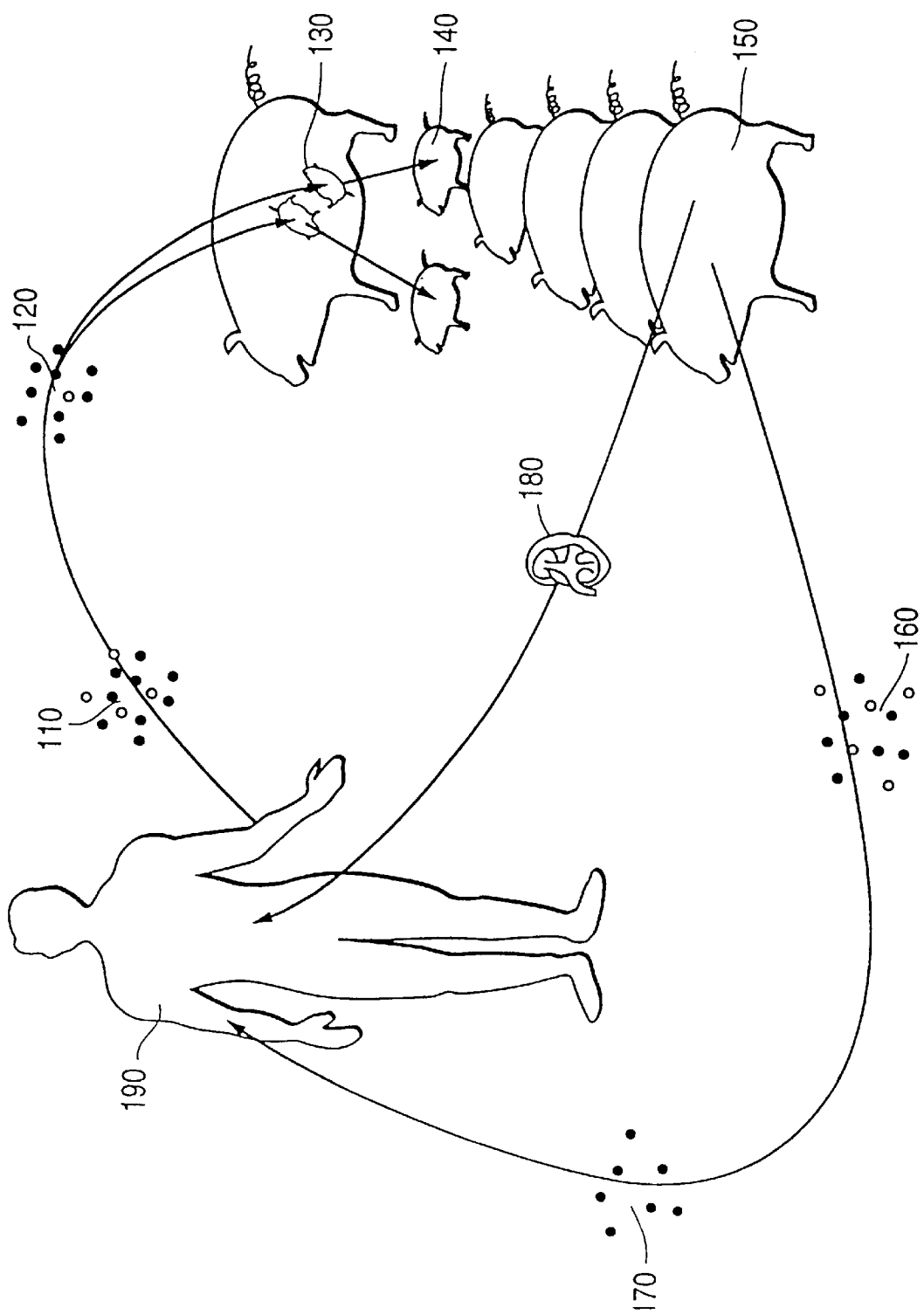
FIG. 1 illustrates one embodiment of the invention by means of a flow chart showing the transfer of lymphoid cells from an organ recipient to a surrogate in the fetal state, where the surrogate later serves as a source of both tolerance-inducing immunosuppressive moieties and a transplant organ.

An organ graft is herein defined to mean a solid organ or tissue to be transplanted.

An organ graft recipient is defined herein to mean an animal such as a human intended to be the final recipient of an organ graft.

A surrogate is defined herein to mean a surrogate animal intended to have organ recipient hematopoietic cells and lymphocytes develop within the surrogate animal. The surrogates are chimeras; i.e. animals engrafted or infused with organ graft recipient cells. These cells and resulting factors develop immune tolerance to the tissues of the surrogate animal, for subsequently transferring back to the organ recipient. The surrogate may also provide the organ graft. The surrogate is always allogeneic, meaning genetically non-identical to the recipient, and usually xenogeneic, meaning of a species different from the recipient.

Lymphocytic progenitor cells, as discussed herein, are defined as lymphocytes that are not fully differentiated. These lymphocytic progenitor cells may be contained in a cell population made up of a variety of cells. A cell population containing lymphocytic progenitor cells would include one or more of the following cell types: hematopoietic stem cells, prethymocytes, early thymocytes, pre-B cells and early B cells. Preferably, this population would exclude antigen reactive memory T cells, antigen reactive memory B cells, and plasma cells. Further discussion of lymphocytic progenitor cells and their role in the differentiation of T and B cells can be found in P. W. Kincade and J. M. Gimble, "B Lymphocytes", in Fundamental Immunology, W. E. Paul, ed., Raven Press Ltd., New York 1989, pp. 41–67 and J. Sprent, "T Lymphocytes and the Thymus", in Fundamental Immunology, W. E. Paul, ed., Raven Press Ltd., New York 1989, pp. 69–93, incorporated herein by reference.

Antigens are defined in Rosen F. S., et al., eds., Dictionary of Immunology, 1989, Macmillan Press, UK, p. 13, as "substances that can elicit an immune response and that can react specifically with the corresponding antibodies or T cell receptors. An antigen may contain many antigenic determinants." Antigenically identical substances, as discussed herein, contain the same antigenic determinants and are reactive with the same antibodies and T cell receptors. Antigenically similar substances, as discussed herein, share many of the antigenic determinants and react with many of the same antibodies and T cell receptors.

Immune response, as discussed herein, includes antigen-induced proliferation of T and/or B lymphocytes specific for the inducing antigen.

Immunosuppressor moieties, as discussed herein, are molecules or cells that specifically inhibit the immune response to a select antigen but do not inhibit the response to other antigens. Examples of immunosuppressor moieties include anti-idiotype antibodies and immune regulatory cells such as suppressor cells, veto cells and antigen presenting cells deficient in surface expression of B7 or related molecules.[1]

Immune competence, as discussed herein, is defined as the ability to mount a normal immune response to antigenically distinct molecules, cells or tissues, but immune competent animals may exhibit decreased response to tolerogenic moieties such as molecules, cells, or tissues antigenically similar to the animal. An example of immune competence would be the ability to promptly reject a skin graft from an allogeneic donor (typically in 6 to 12 days) but accept a syngeneic or autologous graft indefinitely.

[1]B7 is a ligand for T cell surface antigen CD28 that is expressed by antigen presenting cells such as activated B cells, activated monocytes, and dendritic cells. Antigen presentation by MHC class II molecules on cells that express B7 induces optimal T cell proliferation and cytokine production, but antigen presentation by MHC class II molecules in the absence of B7/CD28 binding results in tolerance to the antigen. Gimmi, et al., PROC. NATL. ACAD. SCI. USA, Vol. 90, July 1993, pp. 6586–6590.

Immune deficiency, as discussed herein, is defined as an impairment of the immune reactions to antigenic moieties such as molecules, cells or tissues, as compared to immune reactions of a normal mature animal. An example of an immune deficiency would be an animal that accepts a new skin graft from an unrelated donor for a prolonged period, as compared to first-set rejection in a normal host. Immune deficiency is distinct from immune tolerance. A tolerant animal would demonstrate decreased immune responses to particular molecules, cells, or tissues similar or identical to moieties used to induce tolerance, but would react normally with third party unrelated antigens. Within the current context, examples of immune deficient animals would include fetal animals and animals after total body lethal irradiation. Fetal animals are unable to reject antigens such as cells from the organ recipient because the immune system is immature. Lethally irradiated animals are immune deficient and unable to reject antigens such as cells from the organ recipient because the immune system was destroyed by the irradiation.

Infectious agents, as defined herein, are agents that may infect the recipient of the organ graft or its cells, resulting in injury to tissue. Infectious agents are generally pathogenic entities that may be found in biological samples such as cell populations collected from a surrogate animal. Infectious agents include, but are not limited to, bacteria, viruses, fungi, parasites, mycoplasma and Microsporidae.

Surrogate Tolerogenesis

Surrogate tolerogenesis refers to the production, outside of the intended organ graft recipient, of lymphocytes and soluble factors specifically tolerant to the surrogate animal. For implementing surrogate tolerogenesis, tolerant lymphocytes and factors are developed within the surrogate animal. For example, human cells, including lymphocytes and the appropriate antigen presenting cells (APC), from a human organ graft recipient requiring a transplant (e.g., a kidney) may be infused into surrogates such as fetal pigs. The human cells then become tolerant to the pig antigens. Because the human cells also express the human histocompatibility antigens, the human cells remain tolerant to these human antigens. Later the human lymphocytes and factors from the pig are transplanted back to the organ graft recipient, followed by the transplantation of the pig kidney.

Alternatively, lymphocytes and APC from a prospective donor are mixed with similar cells from the prospective organ recipient and cultured within a third party surrogate fetal animal, allowing for the development of tolerance to adult donors within an environment conducive to the development of tolerance. For example, for a parent wishing to donate a kidney to their child, the organ graft recipient child normally rejects the graft because of a haplotype antigen difference, so considerable immune suppression is normally necessitated to prevent rejection. However, using surrogate tolerogenesis of the present invention, the donor parent's lymphocytes and APC are mixed with similar populations from the organ graft recipient child, and the mixed lymphocytes and APC are transfused into a third party fetal surrogate; for example, fetal pigs. Cultured in the fetal pigs, the lymphocytes and factors of the intended organ graft recipient; i.e. the child in the above example, become tolerant to the antigens of the donor; i.e. the parent. After removing and separating the organ graft recipient lymphocytes and factors from the surrogate, and after transferring the separated organ graft recipient lymphocytes and factors back into the organ graft recipient child, the organ graft recipient child accepts the donor parent's kidney with significantly less risk of rejection and therefore less need for immunosuppressive therapy.

The key to surrogate tolerogenesis is the induction of immune tolerance to donor animal tissue in a population of an organ recipient's lymphocytes and factors, with the induction of the immune tolerance occurring within the surrogate animals. Instead of inducing the human regulatory cells and factors in the organ graft recipient, the regulatory cells and factors are produced outside of the intended organ graft recipient in surrogate animals. Since the organ graft recipient cells differentiating within the surrogate animal also carry organ recipient antigens, the differentiated cells and factors should be immune tolerant to both the organ graft recipient and to the surrogate organ to be transplanted. Organ graft recipient regulatory cells and factors are produced and expanded to provide a tolergenic composition capable of inducing antigen-specific immune tolerance in an organ graft recipient. The composition is a cell population containing regulatory cells and factors which may include suppressor T cells and related suppressor cells, veto cells, subpopulations of B cells, select populations of B cells with surface anti-idiotype immunoglobulins, circulating anti-idiotype immunoglobulins, and select immunoglobulins.

In addition to providing for the production and expansion, harvest, quantitation, and use of immunosuppressor moieties, antigen-specific regulatory cells and serum factors responsible for immune tolerance, including, but not limited to, suppressor T cells and related suppressor factors, veto cells, select populations of B cells with surface anti-idiotype immunoglobulins, and circulating anti-idiotype immunoglobulins, the present invention provides for measuring the regulatory cells and factors responsible for antigen specific immune tolerance prior to their introduction into the organ graft recipient, as well as an opportunity to test the level of tolerance prior to actual transplantation. The present invention also includes producing and monitoring organs and tissues modified for transplantation by the repopulation of the organs with endothelial cells, monocytic cells and leukocytes from the intended transplant organ recipient or with cells from the same species as the organ recipient. The use of the regulatory cells and factors as well as the modified organ graft provides for long term survival of organ grafts, including xenografts, with significantly less immune suppression required for preventing rejection.

The present invention differs from bone marrow transplantation using transgenic cells containing genetic code for donor antigens, in that tolerance to the organ graft develops in the surrogate animal before transplant, thus avoiding the need for lethal chemotherapy and irradiation and marrow transplantation. In addition, use of transgenic cells encoding donor antigens would differ from the present invention in two significant ways. First, it would lead to repopulation following the transplant whereas the present invention would repopulate the organ prior to transplant. Second, it would repopulate the organ with cells containing both donor and recipient antigens, whereas the present invention repopulates the graft with cells that contain only organ recipient antigens.

Although the concept of neonatal tolerance is quite familiar to those knowledgeable in the art, the only clinical application of neonatal tolerance suggested to date has been for transplanting organs and tissues into human fetuses or newborns. The present invention uses the neonatal environment to program suppressor and veto cells and factors to facilitate the transplantation of organs into recipients at a later stage of development, even adult organ recipients.

Instead of attempting to induce tolerance directly in the transplant organ graft recipient, acceptance of non-identical grafts is promoted by inducing tolerance in the organ graft recipient's immune system by means of immune regulatory moieties produced within a surrogate animal by a method termed herein as "surrogate tolerogenesis". This method could also induce the organ graft recipient's cells to tolerate cells of another organ donor, if that donor's tissues or cells are also placed within the surrogate animal. The suppressor or regulatory cells and factors for blocking immune responses to the surrogate or organ donor antigens are cultured in, expanded, and harvested from the surrogate. After transferring the suppressor or regulatory cells and factors to the organ recipient, the recipient accepts an organ graft from the surrogate or donor with significantly less risk of rejection and with significantly less need for immune suppression.

The use of surrogate animals for developing immune tolerance provides the flexibility to perform procedures considered either impractical or unethical if applied to the organ graft recipient. For example, fetal animals may be used as the surrogates even though the recipient intended to receive the transplant is an adult. In the case of xenografts, the use of inbred syngeneic strains may permit the development of tolerance to organs from one individual using another individual as the source of immunosuppressive moieties. Multiple surrogates may be infused, and the surrogate providing the best tolerance may then be selected for harvesting the tolerant cells and factors. The surrogate chimeras may be challenged with fresh organ recipient lymphocytes; i.e. the surrogate chimeras may be exposed to further infusion of fresh organ recipient lymphocytes, and in this manner, the regulation of the organ recipient's lymphocytes by the immune systems of the chimeras will be tested. The surrogates in which the organ graft recipient cells fail to suppress the reaction of organ graft recipient cells to surrogate tissues develop GvHD. On the other hand, the surrogates with tolerant cells and factors from the organ graft recipient prevent the fresh lymphocytes from causing GvHD. In fact, the challenge may expand the responsible cells and factors in the chimeras. Finally, if the monitoring assays indicate that none of the surrogate animals developed tolerant lymphocytes and factors, the subsequent transplant of the organ graft can be postponed or cancelled. This would save the organ graft recipient from the morbidity and mortality associated with a organ graft that was rejected.

Selection of the Surrogate

The principle of neonatal tolerance has been widely observed in various animal species. The infusion of hematopoietic cells into preimmune fetuses has led to chimerism without graft-vs-host disease. The host is then tolerant to the infused cells and the infused cells are tolerant to the host. This has been observed in cows, sheep, pigs, monkeys, mice, rats, and chickens (Owen, SCIENCE, 102:400, 1945; Zanjani, et al., J. CLIN. INVEST., 89:1178–88, 1992; Duncan, et al., TRANSPLANT PROC., 23:841–3, 1991; Hasek, CESK. BIOL., 2:265–70, 1953). The fetal period for developing immune tolerance can be readily established employing the methods described in these papers. The development of suppressor cells can be readily assayed using the methods described elsewhere in this disclosure.

Many animals can potentially be used as surrogates and different animals offer advantages for select uses. Preferred animals are mammals and of the 39 major orders of the class Mammalia, five orders appear particularly suitable as surrogate animals for human organ recipients: primates, artiodactyls, carnivores, rodents, and lagamorphs.

The primates, other than human, are the most suitable animals for surrogate tolerogenesis from the standpoint of organ function. Amino acid sequencing of proteins typically demonstrate 90 to 98% homology with humans. Organs such as livers and hearts function well when transplanted into humans. The primates are concordant with humans, i.e., human recipients do not typically have preformed antibodies to the tissues of the primates.

While some of the lower primates, such as lemurs, have short gestation periods (132–134 days), the higher primates (chimpanzees, gorillas) have gestation periods approximating that of humans (267 days). Intrauterine infusion would be useful for the transplantation of single cells or tissue fragments such as hepatocytes or islets of Langerhans which can be harvested from the fetus or newborn for transplantation. For solid organs (heart, kidney, etc.), however, it would be more practical to induce tolerance in the surrogate by bone marrow transplantation because of the prolonged maturation period.

The artiodactyls, even toed ungulates, include several domesticated animals such as pigs, sheep, goats, and cows. Organs or proteins from several members have been demonstrated to be functional and useful in humans or have been proposed for transplantation. For example, porcine and bovine insulin, pig skin, sheep hearts, etc. have been used or proposed for therapeutic use.

The gestation periods vary between the members of this order. Pigs have a period of 114 days. Sheep have a period of 145 days. Cows have a gestation period of 282 days. As described herein, human lymphocytes have been cultured within fetal pigs and induced antigen specific suppressor cells that suppress the reaction of fresh lymphocytes from the patient to that pig. Human lymphocytes have also been cultured within fetal lambs and have led to stable chimerism. The mechanism of tolerance has not been established for humansheep chimeras, although human lymphocytes differentiate into CD4+ and CD8+ T cells, which are capable of becoming suppressor cells. Cows offer some unique features that are potentially useful for surrogate tolerogenesis. The placental blood of all of the littermates is shared. Therefore human cells infused into a single calf should lead to tolerance to all of the littermates. Because of their large size, cattle can provide more pancreatic islets than other animals for transplantation into diabetics. The limited numbers of pancreatic islets harvested from a human pancreas has been a major factor limiting the use of human allogenic transplantation of islet cells.

The carnivores, including dogs, cats, etc., have several features that are potentially advantageous for surrogate tolerogenesis. Many have short gestation periods (cats about 65 days, dogs about 63 days) and the newborn are relatively well developed. The canine and feline immune systems are very similar to the human immune system. Indeed, the feline immunodeficiency virus model in cats is one of the few animal models available for the study of AIDS. Following bone marrow transplantation, suppressor cells have also been identified in dogs.

Cats and dogs have been commonly used as large animal models for transplantation, including bone marrow, lung, intestine, and bone transplants (Ladiges, et al., LAB. ANIM. SCI., 40:11–15, 1990; Henry, et al., AM. J. VET. RES., 46:1714–20, 1985). Human islets of Langerhans and hepatocytes have been shown to function well in dogs (Calafiore, ASAIOJ, 38:34–7, 1992; Petruzzo, et al., TRANSPL. INT., 4:200–4, 1991; Sussman, et al., HEPATOLOGY, 16:60–65, 1992). It may be anticipated therefore that canine islets and hepatocytes would function similarly in human recipients.

The rodents, including rats, mice etc., are potentially useful for surrogate tolerogenesis because of their short gestation periods and rapid growth to maturity. For example, rats have a gestation period of only 21 days and grow to maturity in only 6 weeks. Because the immune system of rodents is very immature at birth, tolerance can be induced by injecting cells within 24 hours of birth rather than by intrauterine injections.

Because of the short gestation and maturation periods, rodents are particularly useful for generating new strains and transgenic animals. These advantages can be utilized for surrogate tolerogenesis. For example, the SCID mouse could be used for the culture and differentiation of human lymphocytes. Human cell lines have been cultured within nude mice. Using transgenic mice that produce human insulin or mice with cultured human cells, lymphocytes that are tolerant to these cells could be produced within a few weeks by infusing human organ recipient lymphocytes into a large number of newborn mice.

The lagomorphs, which includes rabbits and hares, were once considered part of the rodent order but have been recently separated. They share with the rodents a very short gestation period and short maturation periods. Thus, they would also be useful for the development of new strains, including transgenic strains favorable for maturation of human lymphocytes and providing functional organs or tissues. Their larger size would make these animals better surrogate candidates than rodents.

The ideal surrogate species should be phylogenetically close to the intended organ graft recipient. Also, the physiology of the intended graft should be similar to the physiology of the organ graft recipient organ or tissue to be replaced by the graft. Preferably, the organ graft recipient will be concordant with the surrogate; i.e. the organ graft recipient should not have natural antibodies to the surrogate. With the above criteria, the most optimal nonhuman animals for providing organs and tissues for human transplants are the non-human primates. Non-concordant animals being suitable for providing organs and tissues for human transplants include pigs, sheep, cows, dogs, horses, goats, etc.

Additional considerations influence the choice of species for surrogate tolerogenesis. The transplanted graft is to be approximately the same size as the corresponding graft within the organ graft recipient. If tolerance is to be induced within the fetus, the surrogates require a relatively short gestation period, and the surrogates also require rapid growth after birth, in order to provide suitable grafts to humans as soon as possible. Consequently, with the additional considerations described above, pigs are preferable surrogates over primates, because pigs have a gestation period of only 114 days and typically grow to over 59 kg by four months of age. However, if tolerance is induced after bone marrow transplantation or if the surrogate is used in the development of tolerance to organs of a third party animal, then non-human primates are superior to pigs as surrogates.

Although surrogate tolerogenesis could lead to xenograft transplants without genetic engineering as described herein, genetic modifications could significantly enhance and simplify the procedures. Genetic engineering of large mammals is commonly performed, including genetic modifications of sheep, cows, and pigs. Using techniques that are well known to those familiar with genetic engineering, potential genetic modifications could be made that complement surrogate tolerogenesis. Use of genetically modified animals as surrogates is within the contemplation of this invention.

The potential genetic modifications may be divided into two categories: those that complement or facilitate the methods for surrogate tolerogenesis and those that modify the function of the transplanted organ to better address the recipient's disease process.

Although growth factors for lymphocytes are generally species nonspecific, growth factors for myelocytic and monocytic cells (i.e. granulocytes, macrophages, and dendritic cells) such as G-CSF and GM-CSF are typically species specific. These accessory cells are important to lymphocyte sensitization. Therefore, genetically engineered surrogate animals producing growth factors for the organ recipient myeloid and monocytic cells would be expected to have improved differentiation of the corresponding lymphocytes.

The initial studies of surrogate tolerogenesis in pigs showed that the human lymphocytes readily differentiated into CD4+ lymphocytes but only occasionally into CD8+ lymphocytes. Whereas class II antigen is necessary for differentiation of CD4+ cells, class I MHC antigen is necessary for differentiation of CD8+ cells. The porcine class II antigen appears sufficiently homologous to human antigen to allow CD4+ cell differentiation. Class I antigen, on the other hand, may not be sufficiently homologous to the human counterpart. In order to enhance differentiation of CD8+ cells, a common class I antigen (such as A2) could be inserted with the corresponding promoter gene into ova of surrogate animals such as pigs, and the ova used for in vitro fertilization. The resulting offspring, expanded and bred for homozygosity, would then be used for surrogate tolerogenesis.

Because surrogate tolerogenesis makes the transplantation of xenografts more feasible, it would also justify the genetic modification of the surrogate animal or surrogate tissue. The modifications can lead to secretion of pharmacologically important human proteins, make the animal more resistant to infections, and enhance growth of the animals. For example, a strain of pigs producing increased amounts of alcohol dehydrogenase would be useful for liver transplants performed for alcoholic liver disease. Similarly, pigs producing an increased amount of human insulin in the pancreatic islets would be a useful source of tissue for transplantation treatment of either type I or type II diabetes mellitus. Pigs that produce increased amount of human erythropoietin would be useful for kidney transplants into patients with renal failure and anemia. By increasing the number of beta adrenergic receptors, heart xenografts could be produced that are stronger (SCIENCE NEWS, 145:303, 1994). Numerous other alterations that enhance the transplant organ for a particular disease will be apparent to the skilled worker.

Method of Inducing Tolerance Using a Surrogate

The present invention includes a method for inducing tolerance in a transplant organ recipient to an organ graft from the surrogate. The tolerance is induced while the organ graft recipient's lymphocytes and factors are within a developing surrogate, and these prevent later rejection of the organ graft by the organ recipient after the tolerant lymphocytes and factors are transferred back to the organ recipient. Broadly, the method comprises the steps of obtaining a plurality of cells from the transplant organ graft recipient, and culturing the cells in a fetal surrogate to generate cultured cells. The cultured cells are thereby programmed to be specifically tolerant to the graft of the fetal surrogate. The fetal surrogate is allowed to develop into an immune competent individual. The cultured cells are taken from the developed surrogate, and infused into the transplant organ recipient. The organ graft then is taken from the developed surrogate, and transplanted into the transplant organ graft recipient.

More particularly, the present invention provides a cell population containing immune regulatory moieties (immunosuppressor moieties), including immune tolerant lymphocytes and soluble factors, for use in inducing tolerance in a transplant organ recipient. The lymphocytes and factors for inducing tolerance to the organ graft in the transplant organ recipient may be generated by inducing the tolerance while the recipient's lymphocytes and factors develop within a developing surrogate as the surrogate develops immune competence. When the recipient's lymphocytes are transferred from the immune competent surrogate back to the recipient, they reduce the likelihood of rejection of the graft organ by the transplant organ recipient. To facilitate understanding of the present invention, particular embodiments have been illustrated by means of flow charts in the accompanying figures.

FIG. 1 illustrates one embodiment of the invention by means of a flow chart showing lymphoid cells 110 from the organ recipient 190 which are treated to produce a cell population 120 with reduced numbers of cytotoxic cells and factors that is injected into one or more fetal surrogates 130. Subsequently, newborn surrogates 140 containing organ recipient cells are born and develop into immune competent chimeric surrogates 150. Newborn 140 and mature 150 chimeric surrogate animals are preferably tested for chimerism, lack of GvHD, and tolerance, so that the optimal member(s) can be selected. Lymphoid cells 160 from the chimeric surrogate contain tolerance-inducing cells and factors 170 which are injected into the organ recipient 190 to induce tolerance to the organ 180 which is subsequently transplanted from the surrogate 150 to the recipient 190.

Figure 2:
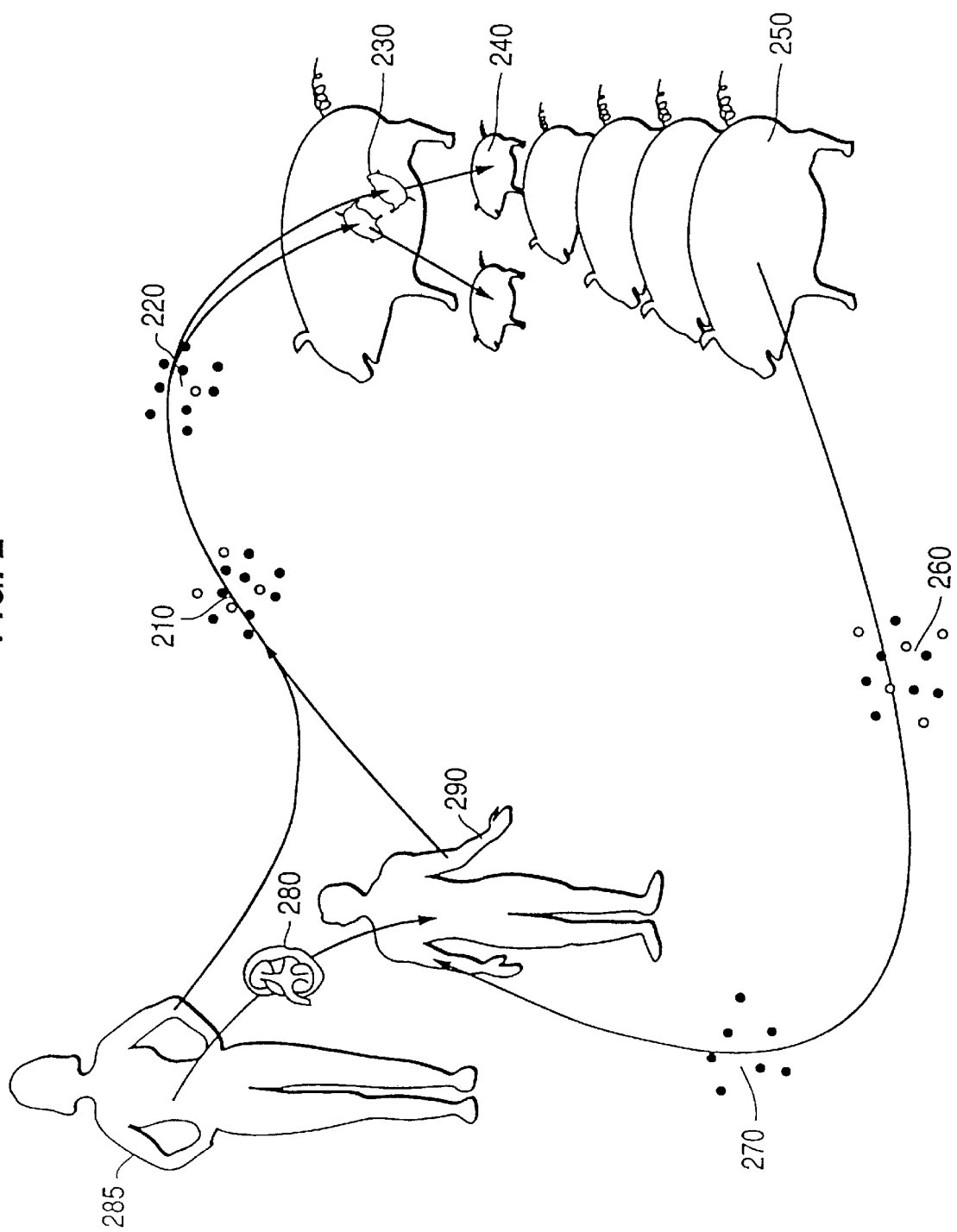
FIG. 2 is a flow chart which illustrates another embodiment of the invention, in which tolerance-inducing cells and factors, produced in a surrogate, induce tolerance in the organ recipient to a transplanted organ from a third party donor.

FIG. 2 illustrates another embodiment of the invention in which tolerance is induced in the surrogate to a third party who serves as the organ donor. A combined population of lymphoid progenitor cells 210 from both the organ donor 285 and organ recipient 290 is treated to produce a cell population 220 with some or all of the cytotoxic cells and cytotoxic factors removed. The cell population 220 is introduced into one or more fetal surrogates 230. Chimeric surrogates 240 are born and develop into immune competent surrogates 250. Newborn 240 and mature 250 chimeric surrogate animals are preferably tested for chimerism with the organ graft recipient cells and tolerance of those cells to the organ graft donor 285. Lymphoid cells 260 from the immune competent surrogate 250 contain immunosuppressive moieties 270 which are returned to the organ recipient 290 inducing tolerance to the third party organ 280 which is subsequently transplanted in the recipient 290.

Figure 3:
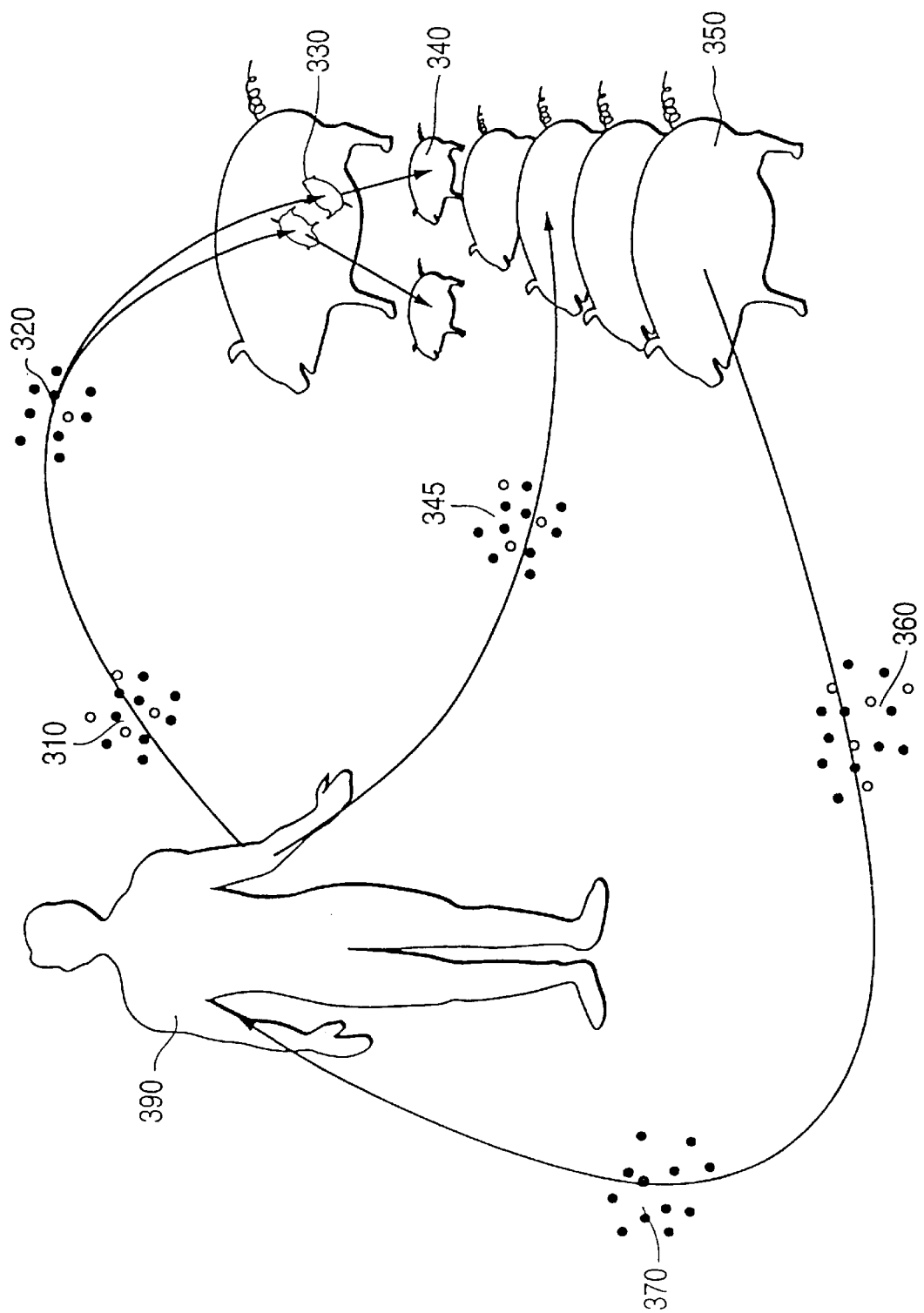
FIG. 3 is a flow chart which illustrates yet another embodiment of the invention, in which the production of tolerance-inducing cells and factors is enhanced by injection of fresh lymphocytes and factors from the organ recipient into the surrogate prior to removing lymphoid cells from the surrogate for transfer to the organ recipient.

FIG. 3 illustrates yet another aspect of the invention in which, after the cell population (with reduced cytotoxic cells 320 derived from lymphoid progenitor cells 310 of the potential organ transplant recipient 390) is administered to a fetal surrogate 330 and the surrogate develops into an immune competent individual 350, a fresh sample of cells 345 from the potential organ recipient is administered to one or more selected surrogate(s) 350. The administration of the second cell population 345 may further expand the immunosuppressive cell fraction in the surrogate providing for greater amounts of immunosuppressive cells and factors 370 in subsequent samples of lymphoid cells 360 from the surrogate. The infusion of cells 345 also tests the competence of the immunosuppressive moieties in the chimeric surrogate.

In one embodiment, the method comprises obtaining a plurality of cells, usually peripheral blood cells or bone marrow cells, as a sample from the transplant organ recipient, and preferably processing the sample to remove mature T cells. The processed sample may also be enriched for immature lymphocytes, immature T cells, stem cells, hematopoietic cells, and antigen presenting cells (APC). The sample (preferably enriched) is infused into a surrogate, when the surrogate is in an immune deficient state, such as a fetal stage of development. Preferably, the sample is infused into a plurality of surrogates. The sample contains lymphocytic progenitor cells which are cultured in the plurality of fetal surrogates as developing T cells of the recipient.

The plurality of fetal surrogates develop to a plurality of developed, immune competent surrogates. As the surrogate develops, the recipient T cells and recipient lymphocytes developing from the lymphocytic progenitor cells are programmed to be specifically tolerant to both antigens of the transplant organ recipient and the antigens of the surrogate tissues. Respective blood samples are taken from the plurality of developed surrogates, and typed to determine the degree of engraftment with organ recipient (e.g., human) cells and to determine the degree of maturation of lymphocytes in the respective blood samples. A biopsy of respective skin samples may be conducted on the plurality of developed surrogates, and in vitro assays conducted on the skin samples.

Transplant organ recipient cells and respective cells within the plurality of developed surrogates are tested for immune tolerance, particularly their ability to regulate the reaction of unprocessed organ recipient cells to donor antigens. Organ recipient lymphocytes are obtained from each of the plurality of developed surrogates, usually from the respective spleens, blood, or lymphoid tissues. The lymphocytes are tested to determine suppression of a proliferative reaction by fresh transplant organ recipient lymphocytes against irradiated cells previously obtained from (or antigenically identical to) the organ donor (i.e., surrogate or third party donor). In response to the step of testing for immune suppression (tolerance), a set of individuals within the plurality of developed surrogates may be selected which are immunotolerant to the organ recipient.

The method preferably includes testing for GvHD induced by grafts of fresh lymphocytes in the respective developed surrogates of the selected set to determine the degree of tolerance conferred by programmed lymphocytes. For example, fresh lymphocytes may be taken from the transplant organ recipient, and infused into the selected set of surrogates. If the organ recipient lymphocytes and factors residing in the surrogate are tolerant to the surrogate tissues and suppress the immune reaction of the fresh organ recipient cells to the surrogate, then they should prevent GvHD by the freshly infused organ recipient lymphocytes. Such an infusion of fresh recipient lymphocytes also may expand the population of human suppressor T cells, veto cells, and anti-idiotype antibodies in the optimal set of surrogates. After testing for GvHD, and before infusing the surrogate-produced, recipient lymphocytes back into the recipient, the method may include selecting from the selected set a best surrogate to serve as the preferred source of immune suppressive moieties and optionally of the organ graft.

Once a chimeric surrogate animal engrafted with recipient cells which suppress the immune reaction of the recipient to the donor has been identified, an adoptive transfer of cells from the surrogate to the recipient is made. Before the step of infusing back the recipient lymphocytes from the surrogate into the transplant organ recipient, the method may include preparing the transplant organ recipient by removing natural antibodies of the organ graft recipient (for example, with plasmapheresis and splenectomy) and/or by infusing soluble complement receptors to block hyperacute rejection of the organ graft.

After infusing the human lymphocytes back into the transplant organ graft recipient, the method may include confirming, by in vitro assays, the degree of tolerance of the transplant organ graft recipient to the antigens of developed surrogate tissues. Specific immune tolerance of the transplant organ graft recipient to the antigens of the surrogate animals is confirmed using assays such as those described herein. A suppression of a proliferative reaction of fresh transplant organ graft recipient lymphocytes obtained after infusion of cells from the surrogate against cells of one or more developed surrogate animals is determined; and an optimal surrogate animal is selected based on greatest suppression. In addition, using in vitro assays, the immune tolerance of the transplant organ graft recipient to cells of the surrogate animals is confirmed.

The best choice among the surrogate animals or the potential pool of donor animals is selected to obtain the graft for the xenograft recipient. The xenograft recipient may be prepared for the transplant by removing natural antibodies to the developed surrogate animals to allow engraftment. The organ graft, preferably obtained from the developed surrogate determined to be the best source, is then transplanted into the organ graft recipient.

Surrogate tolerogenesis as disclosed herein, includes three basic phases or components:

1. Transfer of an organ graft recipient's lymphocytes and APC into at least one surrogate; usually, by transfusion into a number of surrogates;

2. Monitoring development of tolerance within the surrogates and selection of the best surrogate; and 3. Adoptive transfer of tolerant lymphocytes and factors, and usually a corresponding organ graft, from the best surrogate into the organ graft recipient. These three phases will now be described in greater detail.

Transfer of Organ Recipient Cells to Surrogate

The first component includes transplantation of the organ graft recipient lymphocytes and APC into a number of surrogates by infusing, in the preferred embodiment, the organ recipient lymphocytes and APC into fetal surrogates. Either hematopoietic stem cells, marrow, or blood are infused into the abdominal cavities or thymus of a fetal animal, with the infusion optimally performed near the end of the first trimester or during the second trimester of gestation of the surrogates. Preferably, marrow or blood is partially depleted of reactive T cells.

An alternate approach includes performing bone marrow transplantation on the surrogates. The surrogates receive either lethal total body irradiation or high dose chemotherapy to destroy the surrogates' immune system. The organ recipient lymphocytes and APC are preferably either treated to partially deplete the T cells or enriched for hematopoietic stem cells. The treated or enriched lymphocytes and APC are then infused into the surrogates.

Reduction in the number of organ recipient T cells in the infusion may be necessary in either approach to avoid fatal graft-vs-host disease of the surrogate or rejection of the cells from the organ donor. Most preferably, enough T cells should be restored to or retained in the infusion to overcome resistance to engraftment. Generally about 25% to 50% of the original number of T cells, will be sufficient. Preferably, the infusion will contain about 0.1 to $4\times10^8$ T cells per kilogram bodyweight of the surrogate (kg b.w.), most preferably about 1 to $2\times10^8$ T cells/kg b.w.

In fetal animals, at least about $1\times10^8$ nucleated cells/kg b.w., or $1\times10^2$ stem cells/kg b.w. from the organ recipient or from each of the organ donor and recipient should be supplied, and preferably, the fetus should receive 10 to 100 times this number of cells. In irradiated surrogate animals (as in a bone marrow transplant, BMT) $1\times10^8$ nucleated cells/kg b.w., or $1\times10^2$ stem cells/kg b.w. from the organ recipient should be infused, and preferably, the surrogate should receive 10 to 100 times this number cells as well as a mixture of surrogate hematopoietic cells constituting approximately 10% of the total. In third party BMT, $1\times10^8$ nucleated cells/kg, or $1\times10^2$ stem cells/kg b.w. from both the organ donor and organ recipient should be infused, and preferably, the surrogate should receive 10 to 100 times this number cells as well as a mixture of surrogate hematopoietic cells constituting approximately 10% of the total.

The proliferation and differentiation of the organ recipient cells within the surrogates may optimally be enhanced by incubating the organ graft recipient cells in growth factors prior to infusion into the surrogates. For example, the cells could be incubated with recombinant human GM-CSF, IL1, IL3, IL6, IL7, growth hormone, or insulin-like growth factors. The cells could be incubated with a combination of factors. The cells could be incubated with factors or products obtained from fetal tissues such as human fetal thymus. Alternatively, select growth factors or inhibitory factors may be administered to the chimeric surrogates, with the select growth factors being species selective for the organ recipient, and with the inhibitory factors being species selective for the surrogates.

The principal goal of the first component is the induction of antigen specific regulatory cells and factors responsible for tolerance of the organ graft recipient's immune system to the surrogate antigens (or organ donor antigens) by intrauterine induction of tolerance in fetal surrogates or in surrogates which are marrow recipients. The antigen specific regulatory cells and factors are to be capable of blocking or inhibiting the reaction of differentiated organ graft recipient lymphocytes and factors to the organ donor cells. Therefore, the induction of antigen specific tolerance enhances the development of suppressor or regulatory T cells and associated factors, veto cells, enhancement factors and anti-idiotype antibodies.

In order to achieve the induction of antigen specific tolerance, long term survival of the organ graft recipient lymphocytes and antigen presenting cells in the surrogate must be attained without the development of GvHD.

The following examples illustrate preferred embodiments of the present invention, with the organ graft recipient being a human transplant candidate and the surrogates being fetal pigs.

EXAMPLE 1

A 450 ml unit of peripheral blood is removed from the organ graft recipient. Alternatively, a unit of bone marrow (20 ml) may be aspirated. After filtering, the obtained cells are centrifuged and the buffy coat of the cells is saved. The buffy coat includes lymphocytes and antigen presenting cells. The cells are centrifuged through Ficoll-Hypaque to remove red cells and non-viable cells. In order to prevent lethal GvHD in the surrogate, T cells are partially depleted from the suspension. This could be done using rabbit anti-human T cell antibody and baby rabbit complement, as discussed in T. M. Crombleholme, M. R. Harrison, and E. Zanjani, *J. Ped. Surg.*, 25:885–892, 1990. Alternatively, a portion of the cells could be depleted of T cells by incubating them with biotinylated antibodies to CD4 and to CD8, followed by passing them through a cell separation column consisting of beads with bound avidin (CellPro, Inc.). In order to enhance engraftment, additional T cells from the organ graft recipient preferably are added back to the suspension, adding up to 25%–50% of the original number of T cells or alternatively 0.1 to $4\times10^8$ T cells/kg b.w. The suspension may be incubated with recombinant human IL-3 and GM-CSF for enhancing the proliferation of hematopoietic cells, including antigen presenting cells. The suspension may be incubated to generate T cells using additional growth factors to enhance proliferation of early T cells and thymocytes, including recombinant human IL-7 factors and insulin-like growth factor I, also known as somatomedin C.

A midline incision is performed on a sow with a timed pregnancy during the first or second trimester, with the second trimester generally occurring between 38 and 76 days. Preferably the incision is made between 42 and 54 days. The uterus is externalized. Using ultrasound guidance, the treated cells are injected into the abdominal cavities of the identified fetal pigs. The number of cells infused will preferably be between $1\times10^8$ and $1\times10^{10}$ nucleated cells per kilogram of estimated fetal weight. Optionally, radiopaque dye may be included in the suspension to mark the infused fetal pigs.

The surrogates are monitored for up to two months after birth for chimerism, absence of GvHD, and tolerance of organ graft recipient cells and factors to the surrogate antigens. A best or most optimal surrogate pig is chosen from the surrogates, and the organ graft recipient cells and factors are harvested from the best surrogate pig.

EXAMPLE 2

In situations where the culturing of the organ graft recipient cells in the surrogate fetus is not feasible or successful, the cells may alternately be cultured in the surrogate after obliteration of the surrogate marrow and lymphoid tissues with high dose chemotherapy or total body irradiation. Bone marrow transplantation includes the advantage of a greater degree of chimerism and possibly a shorter waiting period. Because bone marrow transplantation does not require a short gestation period or rapid development, bone marrow transplantation may readily be used with other surrogate species, including nonhuman primates. The disadvantages of bone marrow transplantation include requiring a greater total quantity of organ graft recipient cells, resulting in fewer treatable surrogates for a given amount of organ graft recipient cells. Therefore, fewer surrogates result for selection of the best or most optimal surrogate.

Having collected and processed blood or bone marrow from the organ graft recipient by the method described above, the surrogate piglets, being less than three months of age, are treated with either total body irradiation; for example, 1000 R from a $^{137}$Cs source in fractionated doses, or treated with high dose chemotherapy; for example, 200 mg/kg. of cyclophosphamide and 16 mg/kg of busulfan. One day after completion of the irradiation or chemotherapy, treated cells from the organ graft recipient are infused intravenously into the surrogate pigs in doses of $2\times10^8$ to $2 \times 10^{10}$ cells/kg. Optionally, the organ graft recipient cells may be mixed with pig cells harvested prior to irradiation or chemotherapy at a ratio from 1:1 to 10:1 organ graft recipient cells to surrogate cells. Following organ graft recipient bone marrow transplantation to the surrogates, the surrogates may be treated with a short course of low dose immunosuppressive agents to prevent GvHD, with the short course including Cyclosporine, FK506, Rapamycin, Cyclophosphamide, etc. The development of tolerance may be enhanced with post-drug growth factors, including insulin-like growth factor I, also known as somatomedin C. Chimerism, tolerance, including suppressor cells and factors, and lack of GvHD are monitored as described previously. When antigen specific tolerance is established, generally one to six months post-marrow transplant, the optimal surrogate animal is selected. Organ graft recipient cells are harvested and transferred back to the organ graft recipient. After confirming tolerance in the organ graft recipient, the organ graft from the surrogate is removed and transplanted into the organ graft recipient.

EXAMPLE 3

Although the use of humans as surrogates is neither practical nor ethical, non-human surrogates may be used to culture and incubate marrow, lymphocytes, and antigen presenting cells from a prospective third party human donor as well as cells from the organ graft recipient, allowing the organ donor's cells and the organ recipient cells to develop mutual tolerance before the subsequent transfer of the cultured organ graft recipient lymphocytes and factors from the surrogate back to the organ graft recipient. This would be followed by the donor organ.

Blood or bone marrow from the intended organ graft recipient and nonidentical donor are collected and treated as described above. The cells from the organ graft recipient and the organ donor are mixed at a ratio of 1:1 to 10:1 organ graft recipient cells to donor cells, and the mixed cells are infused into the fetal surrogates or mixed with surrogate cells and infused into the surrogates after chemotherapy or total body irradiation. The surrogates are monitored later for chimerism of the organ graft recipient cells, and for tolerance of the organ graft recipient cells and factors to the third party organ donor's antigens. GvHD against the surrogate is irrelevant for developing tolerance between the organ graft recipient's cells and the third party organ donor's antigens.

EXAMPLE 4

Immune tolerance to all siblings of a surrogate organ donor can be achieved by infusing leukocytes from the mother and the father of the potential organ donor along with the lymphocyte progenitor cells of the organ recipient into the surrogate animal. Because the siblings express histocompatibility antigens derived from either parent, tolerance to both parents would provide tolerance to each of the siblings as well. As an example, at the time of infusion, between $1 \times 10^7$ and $1 \times 10^{10}$ lymphocytes/kg body weight from each parental pig is infused into the fetal pig along with $1 \times 10^7$ to $1 \times 10^{10}$ lymphocytes/kg body weight from the organ recipient. The parental cells may optionally be irradiated (500 to 4000 rads, optimally 1500 rad) or the number of T cells reduced to prevent rejection of the organ recipient cells, the other parental cells, or graft-vs-host disease against the surrogate animal being infused. Subsequently, transplant organs may be used from other members of the litter if the infused surrogate has the same parents, from a previous litter by the same parents, or from members of litters unrelated to the surrogate animal if the parents are unrelated to the infused surrogate animal.

Inducing tolerance to all parental antigens provides two practical advantages. First, this would allow for pooling of tissues from the littermates. For example, a major factor limiting the success of pancreatic islet transplants for the cure of diabetes mellitus is that typically too few islets are harvested from a single donor. Once tolerance to all of the littermates is achieved, however, islets from multiple or all of the littermates can be pooled, providing sufficient islets for successful transplant, making the patient insulin independent Secondly, tolerance to all parental antigens allows organs to be transplanted from a previous litter of mature surrogate organ donors. In the embodiment of the invention in which the surrogate is the organ donor, the transplant must be delayed until the surrogate animal has matured sufficiently that the xenograft, such as a kidney or heart, is large enough for the organ recipient. For pigs, the wait could be reduced from six or seven months to just two or three months by using parental antigens in the tolerogenic stage.

Similarly, primates could potentially be used as surrogates or donors. In the embodiment in which the surrogate is the organ donor, the non-human primate would require many years of maturation, making it impractical. By inducing tolerance to parental antigens, however, the wait could be reduced to a few months. For example, cells from maternal and paternal parents of a mature baboon can be infused, along with the organ recipient's cells, into a fetal pig. After birth of the pig, the suppressor cells and factors are harvested from the pig and transferred into the organ recipient. An organ from a mature offspring member of the parent baboons can then be transplanted into the organ recipient.

Inducing tolerance to the F1 generation by infusing parental cells offers some practical advantages over using inbred strains of animals. Outbred animals generally are more robust than inbred animals. Although an inbred strain of pigs exists, there are no inbred strains of higher animals such as non-human primates.

Where the lymphocyte progenitor cells from more than one individual are infused into the surrogate (e.g., lymphocyte progenitors from donor and recipient, from both parents of the donor, or from a set of animals representing multiple tissue types of the recipient's species) the lymphocyte progenitor populations from the various individuals should be infused substantially contemporaneously. In this context, the infusions are considered substantially contemporaneous if all of them occur while the surrogate is still in a state of immune deficiency, although typically the various progenitor populations will be infused sequentially in a substantially continuous infusion, or the populations will be mixed together before infusion and thus infused simultaneously.

Monitoring Surrogate Development

The second component of surrogate tolerogenesis involves the monitoring of chimerism and tolerance within the surrogates and involves the selection of the best or most optimal surrogate from the number of surrogates. Following fetal culture or bone marrow transplantation, the surrogates are monitored to establish chimerism; i.e. expansion and maturation of the lymphocyte populations and factors from the organ graft recipient within the surrogate, as well as tolerance of the lymphocyte populations and factors to the organ donor antigens. The assays used to select the best or most optimal surrogate chimera for providing tolerant lymphocytes and factors and for providing the best suited factors will be readily apparent to the skilled worker. Assays may be selected from those taught below.

The monitoring involves a quantitation of the extent of chimerism in the surrogates; i.e. the relative numbers of organ recipient cells within the surrogates, and monitoring of the tolerance for the organ recipient cells towards the surrogate antigens. Chimerism may be readily followed using flow cytometry and antibodies specific for the surrogate and for the organ recipient species. For example, if the surrogate is a pig, then pig blood and bone marrow may be screened for the relative numbers of human lymphocytes as well as pig lymphocytes. The antibodies may include monoclonal antibodies to human CD45, CD2, CD3, CD5, CD7, CD19, HLA-DR, HLA-ABC, CD45RO, CD45RA, CD4, CD8, CD34, and CD31 as well as to swine CD45, CD2, CD3, CD4, CD8 and swine surface immunoglobulin. The degree of chimerism may also be quantified in lymphoid tissues, including the thymus, the spleen, and the lymph nodes. In a preferred embodiment, the method of the present invention further includes characterizing the extent of chimerism within the tissue to be used as an organ graft. These studies would include immunohistochemistry, such as immune alkaline phosphatase stains of biopsy tissues using antibodies to human factor VIII, dendritic cells, CD45, CD4, CD8, CD2, CD5, HLA-DR, and HLA-ABC.

Immune tolerance of the organ recipient cells, cultured in the surrogate, towards the surrogate organs and tissues may be monitored by a variety of methods. One method of monitoring immune tolerance involves taking biopsies of the surrogates' tissues intended to be grafted, and characterizing the surrogates' tissues for evidence of a rejection process by the recipient cells. Other tissues of the surrogates, such as skin, liver, and intestines, may also be examined for evidence of GvHD. Another method of monitoring involves performing in vitro tests of tolerance, where the in vitro tests may include mixed lymphocyte cultures (MLC) and suppressor cell assays. In such in vitro tests, cultured lymphocytes are added to an MLC of fresh organ recipient responder cells versus irradiated surrogate or organ donor stimulator cells. Because some xenograft pairs may show a limited proliferation, limiting dilution assays may be necessary to establish a reduction in precursor cytotoxic T lymphocytes. An additional method of monitoring involves using flow cytometry and immunohistochemistry studies to provide a relative quantitation of lymphocytes with a phenotype for suppressor cells; for example, antibodies to CD31 may be used. The organ graft recipient cells may also be monitored for a reduction of T cell receptor rearrangements corresponding to lymphocytes reactive against surrogate or organ donor antigens.

The use of surrogates for the development of tolerance provides the opportunity for a novel bioassay for assessing immune tolerance. An advantage of using surrogates as bioassays includes assessing the degree of immune tolerance in the surrogate prior to transplanting the organ graft from a surrogate to a recipient. Chimeric surrogates are infused with fresh lymphocytes from the organ graft recipient, and, if the chimeric animal is truly tolerant, then regulatory cells and factors prevent the fresh lymphocytes from causing either GvHD or immune rejection of the intended graft tissue. The above bioassay using the surrogates is referred to as an "immune challenge". Following the challenge, biopsies may be taken of tissues routinely injured by GvHD, and biopsies of the intended graft tissue can also be taken. Besides monitoring the development of tolerance, the challenge provides a further benefit to the degree that it stimulates the expansion of regulatory cells; for example, the development of additional suppressor T cells may be stimulated.

If the surrogate is also the source of the organ graft, assays for chimerism and determinations of chimerism in cell suspensions are performed on the surrogates. At −1 to 120 months (preferably from zero to four months) after birth of the chimeric animal, or at 1 to 120 months (preferably one to seven months) after bone marrow transplantation, blood and bone marrow specimens are collected from the surrogates. Preferably, the buffy coats of the specimens are isolated, and the cells are stained with antibodies specific for CD45 of the species of the organ graft recipient. The extent of chimerism may be quantified using analytical flow cytometry. Evidence for maturation of T cells may be established using double label flow cytometry for CD4 and CD8, for single positive cells, and expression of CD3. T cells with a phenotype for suppressor cells may be quantified with antibodies to CD31 and optionally Leu15. Maturation of B lymphocytes may be assayed with CD19 and CD21, and macrophages may be assayed with antibodies to CD14, and CD11b. Additional studies may be performed on the best or most optimal surrogates by making cell suspensions of lymph node biopsies, and by making fine needle aspirates of the spleen. Optionally, chimerism may be assessed in cell suspensions using cytogenetics and restricted length fragment polymorphisms (RLFP). Immunopathology of the surrogate tissues may be conducted to establish chimerism and to rule out GvHD and immune reactions to the graft tissue. Immunopathology studies may be performed on biopsies of the skin, the liver, the intestines, the bronchial mucosa, the thymus, the lymph nodes, the spleen, and/or other tissues from the intended graft. These target tissues are stained and evaluated for cellular injury indicative of GvHD or organ graft recipient vs. surrogate tissue injury. Using antibodies specific for subgroups of cells of the organ graft recipient species, immunohistochemistry can establish chimerism with biopsies of lymph node, spleen, and thymus. In general, mouse monoclonal antibodies against human CD45, CD4, CD8, CD3, CD19, CD21, CD31, perforin, HLA-DR, HLA-DQ, HLA-ABC, CD14, CD11b and CD1 are usually used to identify mature T cells, suppressor T cells, B cells, macrophages, and dendritic cells. CD1 also identifies thymic dendritic cells and cutaneous Langerhans cells. Antibodies to factor VIII of the organ graft recipient species typically identify reconstitution of the endothelium with organ graft recipient cells. Sections of tissue are typically incubated with a primary antibody; washed; incubated with a secondary antibody; for example, biotinylated horse anti-mouse immunoglobulin; and developed using the avidin-biotin complex assay. Immunofluorescence stains may be performed for organ graft recipient species immunoglobulins and for deposits of complement of either the organ graft recipient or the surrogate species.

Tests of tolerance for the xenograft are usually conducted. For example, in vitro tests of tolerance may be performed and the relative degree of tolerance established by mixed lymphocyte reactions and suppressor cell assays. Peripheral blood, spleen, and lymph node lymphocytes may be tested in one way MLC's against irradiated stimulator cells harvested from the surrogate. Proliferation is typically assayed after six days, by tritiated thymidine uptake. The degree of tolerance is relative to the reduction in proliferation as compared to an MLC of fresh organ graft recipient lymphocytes against surrogate stimulator cells.

Although xenogeneic MLC's are often less intense than allogeneic reactions, the number of cytotoxic lymphocyte precursor lymphocytes to the target is comparable. Limiting dilution assays therefore may be used to establish the number of precursor cytotoxic cells (CTL) to surrogate antigens. The tolerized organ graft recipient cells would have a reduction in precursor CTL compared to fresh organ graft recipient cells.

The presence of lymphocytes and serum factors for regulating and specifically inhibiting the reaction to surrogate antigens is more important than a reduction in cytotoxic cells. Suppressor cell assays are typically conducted to test the relative ability of the organ graft recipient cells obtained from the surrogate to inhibit an MLC of fresh organ graft recipient cells vs. irradiated surrogate stimulator cells as described above. For example, lymphocytes obtained from the surrogate chimera, depleted of surrogate cells by antibody and complement methods, may be added to the MLC and a reduction in proliferation determined. The absolute number of regulatory cells may be determined using a limiting dilution approach to the suppressor cell assay. Alternatively, if the surrogate is the source of the organ graft, suppression can be assessed by comparing the proliferation observed in a two-way MLC between fresh organ recipient lymphocytes and chimeric surrogate cells to the sum of the one-way MLC's of recipient vs. chimeric surrogate cells and chimeric surrogate vs. recipient cells.

In a similar manner, serum from the chimera, depleted of complement, may be added to an MLC to establish if soluble factors for effectively reducing the MLC reaction are present. A cross match of surrogate serum and organ graft recipient cells may be performed to rule out a trivial reduction resulting from a destruction of the organ graft recipient cells.

The ability of the organ graft recipient lymphocytes and factors to prevent rejection may also be tested using a tissue explant assay. In a typical assay, a biopsy of the intended graft is taken from the surrogate, divided into 1 mm pieces, and placed in a tissue culture. Lymphocytes from an MLC at three days are cocultured with the tissue fragments for 1–2 days. The fragments are then evaluated histologically for evidence of rejection. Alternately, the added lymphocytes may be radiolabelled and the uptake of tagged lymphocytes determined by counting the labelled cells in sections of the specimen using autoradiography. Control assays are conducted involving an MLC of fresh organ graft recipient lymphocytes vs. surrogate stimulator cells and surrogate lymphocyte vs. surrogate stimulator cells. The suppressor test adds the serum factors or regulatory cells from the surrogate chimera to the MLC.

An in vivo test of tolerance may be conducted using the novel assay of taking advantage of the development of tolerance in the surrogate and of challenging the immune tolerance in the surrogate chimera. The in vivo test of tolerance provides a basis for comparing surrogate chimeras and also provides the means for further expanding the regulatory cells and factors responsible for tolerance.

After birth of the surrogate or after the bone marrow transplant (usually at one to four months), blood and bone marrow of the surrogate are preferably examined for chimerism and biopsies performed to rule out an immune reaction against the surrogate tissues. Typically, fresh peripheral blood lymphocytes, in doses of $2 \times 10^8$ to $2 \times 10^{10}$ lymphocytes/kg of surrogate weight, are infused intravenously into the surrogate chimera. The absolute peripheral blood lymphocyte count and the degree of chimerism with organ recipient cells is determined one hour later. Five to 14 days later, the surrogate is again biopsied for evidence of GvHD or immune reactions against the intended graft tissue and the absolute lymphocyte count and chimerism is again determined. If the challenge is successful, the surrogate shows no evidence of GvHD or graft injury. The surrogate may show an increased number of peripheral blood organ graft recipient lymphocytes.

The above procedures are applicable if the intended graft tissue is from the surrogate. If the surrogate is to be the source of the graft, the assays for chimerism are generally the same for surrogate chimeras established in fetuses as for surrogate chimeras created from bone marrow transplants. If, on the other hand, lymphocytes and APC from the intended organ graft recipient and third party organ donor are mixed and cultured within the surrogate, then different procedures may be required to assess chimerism and tolerance. Where the surrogate is to be used for developing tolerance between organ graft recipient and third party organ donor, the assays for surrogate chimeras established in fetuses may differ from the assays for surrogate chimeras created from bone marrow transplants.

Typically, chimerism and tolerance between the surrogate cultured organ graft recipient immune system and the prospective third party organ donor antigens will be determined. When prospective organ graft donor cells and organ graft recipient cells are mixed and cultured within a third party surrogate, either when the surrogate is a fetus or after a bone marrow transplant, the reactivity of the organ graft recipient cells to the surrogate is largely irrelevant. If the organ donor and organ graft recipient are from the same species, the two populations of cells will usually be differentiated.

If the prospective organ graft donor and organ graft recipient differ with respect to sex, then the relative number of male and female cells may be established using fluorescent in situ hybridization (FISH) stains of cells deposited on a slide by cytocentrifugation. Maturation of lymphocyte subsets may be done by double label immunohistochemistry on cytospin preparations. Thus, the relative number of male cell or female cells, depending on the prospective organ graft donor or recipient, being CD3, CD4, or CD8 positive may be determined.

Alternately, if the prospective organ graft donor and organ graft recipient have a detectable MHC difference, double label flow cytometry or immunohistochemistry using antibodies to a respective MHC marker and differentiation antigens may be used to determine the relative degree of chimerism and maturation.

Mixed lymphocyte reactions test the reaction of organ graft recipient lymphocytes (depleted of surrogate and prospective organ graft donor cells) against irradiated fresh organ graft donor stimulator cells. Surrogate and organ graft donor cells may be depleted from the cell suspension using either antibody and complement methods or antibody and immunomagnetic beads. Limiting dilution assays of fresh organ graft recipient cells and surrogate cultured organ graft recipient cells establish the absolute reduction of precursor cytotoxic cells.

Suppressor cell and suppressor factor assays test the inhibition of an MLC consisting of fresh organ graft recipient lymphocytes against fresh surrogate stimulator cells by chimeric organ graft recipient cells.

If the performed assays and tests indicate the presence of both prospective organ graft donor and organ graft recipient cells as well as the establishment of tolerance to the surrogate, an immune challenge may be performed. In a typical immune challenge, fresh organ graft recipient cells are infused into the surrogate. One hour later, the surrogate blood is tested for the absolute cell counts of organ graft recipient type cells and organ graft donor type cells. Five to 14 days later, the surrogate blood is again tested for absolute cell counts of organ graft recipient type cells and organ donor type cells. If the test is successful, then both organ graft recipient cells and surrogate cells remain, but the absolute cell count of organ graft recipient type cells are increased. In vitro tests for tolerance demonstrate that the organ recipient cells are tolerant to the organ donor antigens.

Transfer of Tolerance Factors

The third component begins by having the organ graft recipient cells and factors harvested from the surrogate and preferably enriched for lymphocytes and factors providing tolerance, optionally, after selecting the best or most optimal surrogate based on chimerism and tolerance of the organ graft recipient cells to the surrogate antigens. Lymphocytes and soluble factors are isolated from the surrogate, including the blood, serum, bone marrow, spleen and/or other lymphoid tissues. Bone marrow, spleen, lymph nodes, and/or serum are sterilely removed from the selected surrogate. The lymphoid tissues are usually passed through a wire mesh to produce a suspension of lymphocytes. Preferably, the combined suspension is centrifuged and the buffy coats are saved.

After harvesting the lymphocytes from the chimeric surrogate, the lymphocyte-containing cell population is preferably enriched in organ recipient's cells before being transfused back into the patient. The population of cells and factors may be significantly enriched for organ graft recipient cells and factors by removing most of the surrogate cells, accomplished using antibody and complement methods, antibodies attached to magnetic beads, or an affinity column. If the organ graft recipient cells represent a minor component of the chimera, they can be positively selected using antibodies to organ graft recipient lymphocytes and immunomagnetic beads. Alternately, an immunoadsorption column which retains organ graft recipient lymphocytes can be used. The surrogate cells would pass through while the recipient cells remained attached. Subsequently the organ graft recipient cells would be eluted from the column.

Enrichment may be achieved by adding antibody specific for surrogate leukocytes, such as swine CD45, and complement to destroy surrogate leukocytes. Alternately, the cell suspension may be treated with antibodies to surrogate leukocytes and immunomagnetic beads. The beads attached to the surrogate cells are then removed with a magnet. An adsorption column with attached anti-surrogate CD45 antibody may also remove the surrogate cells. If the surrogate cells differ from the organ graft recipient cells in physical properties; for example, cell density, the surrogate cells may be separated by elutriation centrifugation.

A much simpler separation could, however, be done using genetically engineered surrogate animals. The surrogate's cells can be genetically modified to have a defined disadvantage in cell culture. The recipient's cells would then dominate after a short period of culture. For example, the commonly used marker gene thymidine kinase (KT) may be inserted into pig ova and a strain of KT+ pigs produced. KT+ cells are sensitive to the antibiotic gancyclovir. Human cells do not produce KT and are therefore be resistant to gancyclovir. When the chimeric cells are harvested from the genetically modified surrogate animal, they will be cultured in the presence of gancyclovir. The drug will kill the surrogate cells but not the organ recipient cells, thus enriching the mixture for the organ recipient cells, including the suppressor cells.

The enriched lymphocytes and factors responsible for conveying immune tolerance are then infused into the organ graft recipient. Minimum cell populations are needed for infusion, and the cell number is typically the same as the number infused into immune deficient surrogates. Preferably, between $5 \times 10^8$ and $5 \times 10^{10}$ organ graft recipient cells/kg organ graft recipient weight are obtained following harvest and enrichment. The in vitro tests of immune tolerance described previously may be used to assess the obtained lymphocytes and factors.

Some preparation of the organ graft recipient may be necessary prior to infusion of the enriched lymphocytes and factors to overcome resistance to engraftment. The problem of resistance to engraftment is also encountered and resolved in organ graft recipients treated with genetically altered cells. Even though the lymphocytes and factors are antigenically identical to the organ graft recipient, the lymphocytes and factors may only engraft locally at the site of infusion. The local engrafting may be overcome with modest, sublethal doses of chemotherapy, total lymphoid irradiation or total body irradiation.

In some circumstances, the organ graft recipient may require treatment before the adoptive transfer of organ graft recipient cells harvested from the surrogate, with the treatment including therapy (for example, chemotherapy or sublethal radiation) to allow for reengraftment of the organ graft recipient by cultured cells from the surrogate. If the surrogate and organ graft recipient are discordant; i.e. the organ graft recipient has natural antibodies against the surrogate tissue, additional therapy is required to block a hyperacute rejection of the surrogate tissue. Plasmapheresis, splenectomy, cobra venom factor, and/or the use of soluble complement receptors may be used for the additional therapy. These additional therapy efforts are generally directed at circulating factors in the recipient at the time of transplant; the cells and factors transferred back to the organ graft recipient from the surrogate may prevent the similar development of these factors at a later period.

Humans have high levels of circulating natural antibodies that react with oligosaccharides expressed on the surface proteins and lipids of discordant animal cells. Whereas surrogate tolerogenesis would prevent the cellular rejection of the surrogate organ by the recipient, preformed antibodies need to be eliminated from the recipient prior to transplanting the organ. Recently, genetic engineering has been proposed to produce animals that are better suited for organ transplantation.

For example, human decay activating factor (DAF) has been produced by a herd of transfected pigs. The insertion of human DAF into the ova of pigs produces a herd of animals more resistant to preformed antibodies. This would reduce the destruction of the organ xenograft caused by the binding of natural antibodies and activation of human complement.

Whereas discordant animals produce alpha galactosyltransferase (AGT) responsible for the development of oligosaccharides on discordant animal cells, humans, apes and old world monkeys fail to produce significant amounts of this enzyme. This failure is believed to be due to a mutation in the DNA responsible for AGT (Galili, SPRINGER SEMIN. IMMUNPATHOL., 15:155–71, 1993). A strain of animals such as pigs containing a nonfunctional AGT may be produced using homozygous recombination to insert non-functional code into the pig gene for AGT or the corresponding promoter gene (Watson, et al., "Recombinant DNA," Scientific American Books, N.Y., 1992, pp. 255–72). This alteration in the surrogates cells would be better than administering complement inhibitors to the graft recipient, since the graft recipient's immune system could still interact with infected cells in the organ and protect it. By using genetically modified pigs or other animals with complement inhibiting factors as surrogates, the need for plasmapheresis, ex vivo perfusion, or complement inhibiting drugs such as cobra venom factor could be significantly reduced.

Following adoptive transfer of tolerant lymphocytes and factors from the surrogate to the organ graft recipient, blood drawn subsequently from the organ graft recipient is then evaluated for tolerance against the surrogate tissue using in vitro methods similar to the in vitro methods described above. If the organ graft recipient does not demonstrate significant tolerance, additional transfers of lymphocytes and factors may be performed, including cells from other surrogates. If, on the other hand, satisfactory tolerance is established, then the organ graft recipient receives a surrogate organ or tissue using standard transplant procedures.

Peripheral blood lymphocytes from the organ graft recipient may be tested by MLC tests for tolerance to organ donor cells. If the surrogate is the source of the graft and the organ graft recipient is discordant for the surrogate species, the organ graft recipient is preferably screened for the presence of natural antibodies. If the organ graft recipient is serologically reactive to the surrogate, then the organ graft recipient will usually require additional treatment; for example, plasmapheresis and splenectomy or soluble complement receptors to prevent hyperacute rejection. Because long term stable chimerism may be achieved in discordant pairs, the lymphocytes and factors from the surrogate, as regulatory cells, may prevent the subsequent production of additional natural antibodies.

Organ Transplantation

Once tolerance in the organ graft recipient is confirmed, the graft from the surrogate or donor is transplanted into the organ graft recipient. If the surrogate serves only as an incubator for the development of tolerance-inducing cells, then the graft from the prospective third party organ donor is harvested and transplanted. If the surrogate is the source of the graft, the transplant of the graft may then be performed from the surrogate to the organ graft recipient. Surgical transplantation techniques are well known in the art (see, e.g., Simmons, et al., "Transplantation," in Schwartz, et al., 1989, eds. *Principles of Surgery,* McGraw-Hill, N.Y., pp. 387–458). The organ graft recipient is monitored for evidence of rejection of the organ graft in accordance with routine practice in the art, but the need for immunosuppressive therapy is significantly reduced compared to known methods of transplantation in the art.

If the surrogate has two or more of the graft organs, e.g. kidneys, then the original surrogate may be kept alive as a backup in the event of the first graft failing. Similarly, additional surrogate chimeras may be kept as backups for unique grafts; for example, grafts of hearts, or the additional surrogate chimeras may be kept in the event of failure of immune tolerance.

Transplantation in accordance with the principle of surrogate tolerogenesis as described herein will significantly reduce the incidence of rejection for a multiplicity of solid tissue organs, including skin, heart, kidney, liver, lung, intestines, pancreas, pancreatic islets, retina, cornea, bone, spleen, thymus, bone marrow, salivary glands, nerve tissue, adrenal glands, and muscle. For example, a common cause of visual impairment in the aged is macular degeneration with degeneration of the retinal pigment epithelial cells. After inducing tolerance of the patient to the surrogate animal, the retina of the surrogate animal can be transplanted into the patient with reduced risk of rejection.

Coculture of Lymphocytes and Cell Suspensions in the Surrogate Animal

The principle of surrogate tolerogenesis can also be used for facilitating transplant of organs that are fundamentally populations of cells transplanted as cell suspensions, such as bone marrow transplants (BMT) or insulin-producing cells from islets of Langerhans of the pancreas.

The preimmune fetal environmental leads to tolerance to newly introduced antigens. Infused lymphocytes also develop tolerance to the antigens present, including other infused cells. The fetal environment also allows for proliferation of cell suspensions. By coculturing the putative organ recipient's lymphocytes with cell suspensions from the organ recipient's species, it is possible to provide sufficient cells for subsequent transplant and induce tolerance to these cells in a single procedure.

For example, pancreatic islets harvested from aborted human fetuses (10 to 14 weeks gestation) may be infused with lymphocytes from a patient with type I diabetes mellitus into the abdomens of fetal pigs. At birth, the human lymphocytes are harvested, enriched, and tested for tolerance to the human islets. These cells are infused into the patient. Shortly, thereafter, the expanded population of human islets is harvested and transplanted into the patient. The fetal expansion of islets would provide adequate numbers of human islets. The patient's lymphocytes cocultured with human islet cells would induce immune tolerance of the patient to the allogeneic human islets.

Similarly, a suspension of human fetal hepatocytes could be cocultured with patient's lymphocytes in the fetal pig. Under ultrasound guidance, the hepatocytes could be infused into the prominent hepatic vein of the fetal pigs. Later, this pig would provide a liver transplant partially repopulated with human hepatocytes. The advantages over an unmodified pig liver would include decreased antigenicity and better metabolism.

Cell suspension could also facilitate the development of tolerance in surrogate tolerogenesis. For example, the injection of human thymic epithelial cells could facilitate positive selection and differentiation of CD8+ lymphocytes. The thymic epithelium could be provided from aborted fetuses or from a cultured cell line.

Allogeneic Bone Marrow Transplantation (BMT)

Because bone marrow is a renewable tissue, there is not a shortage of potential human bone marrow donors. Graft-vs-host disease, however, is still a major complication limiting the effectiveness of BMTs. Surrogate tolerogenesis would allow the immune system of the donor to become tolerant to the recipient outside of the recipient. Besides decreasing the risk of GVHD, surrogate tolerogenesis would allow for multiple transplants and selection of the best surrogate animal, would allow the transplantation of a mature immune system, and would allow for immunization against tumor and select infectious agents.

Bone marrow cells from the donor and recipient would be infused together into the surrogate animals, such as fetal pigs. Later, the surrogate animals would be screened for engraftment by the donor cells and for tolerance to the recipient by mixed lymphocyte assays. Donor cells would then be harvested from the best surrogate animal and infused into the bone marrow recipient after appropriate preparation.

Immunosuppressive Compositions

The present invention also provides, in another embodiment, a composition containing immunosuppressive moieties capable of suppressing the immune response to tissues or cells of both an organ graft donor and an organ graft recipient, formulated for infusion into the organ graft recipient. Preferably, the composition will be a cell population which contains immunosuppressive moieties such as suppressor T cells, cells producing anti-idiotype antibodies, veto cells, and/or antigen presenting cells deficient in B7 or similar molecules. Such cells may be obtained from a surrogate animal treated as taught herein by administering a cell population containing lymphocytic precursor cells from the recipient to the surrogate when the surrogate is in a state of immune incompetence and subsequently allowing the surrogate to develop into a state of immune competence exhibiting immune tolerance to tissue of the surrogate and the recipient. The cell population may also contain circulating factors such as anti-idiotype antibodies in addition to the cells.

The cells harvested from the surrogate are preferably enriched for organ recipient cells using positive selection of organ recipient cells or negative selection to remove some surrogate cells or organ donor cells. Positive selection may employ magnetic beads or an adsorption column containing antibodies specific for the organ graft recipient cells. After the desired cells attach to the beads or column, the beads or columns are washed with medium to exclude unwanted cells. The desired cells are then eluted with cold medium or EDTA. Negative selection to remove unwanted cells may employ magnetic beads or adsorption columns with attached antibodies specific for the unwanted cells. The desired cells would be enriched in the non-attached fraction collected after the beads are removed or in the elutrate from the column. Alternately, antibody and complement may be used to lyse the unwanted cells. Preferably, the enriched cell populations will be "substantially free" of surrogate cells meaning that the number of surrogate cells are reduced by 70%, more preferably by 80%, and most preferably by 95%.

Expansion of regulatory cells may be accomplished in vitro using spent culture medium from a mixed lymphocyte culture. A mixed lymphocyte culture (MLC) consists of a culture of lymphocyte and antigen presenting cell populations from two or more allogeneic donors from the same species as the organ graft recipient. The cells are cultured together in cell culture media using standard MLC techniques. The culture supernatant is removed at 18 to 48 hours and added to the cells harvested from the surrogate animal. A similar effect could be achieved using purified or synthesized factors that would be present in this medium.

Harvested and prepared cells may be frozen for later use or shipment to a remote facility using standard cryopreservative techniques, with fetal calf serum and DMSO and programmed cooling to −85 degrees C or lower. Extracted cells are tested for tolerance and autoregulatory cells and factors as well as for neoplasms, viruses, and infectious agents that could be passed on the organ graft recipient. Preferably the immunosuppressive moieties of the composition are formulated for introduction into the recipient according to the methods used in cryopreservation of lymphocytes, as discussed in Venkateraman, et al., *J. Lab. Clin. Med.*, 20:453–458 (1992), incorporated herein by reference. Formulation of the cells for injection is within the skill of the art.

Repopulation of Organ Grafts With Recipient Cells

Another result of surrogate tolerogenesis is the generation of organs repopulated with organ recipient cells, in particular endothelial cells, monocytes and related cells, and other leukocytes. Because the endothelial cells, monocytes, related cells, and other leukocytes are also targets for rejection, replacing the surrogate's cells by repopulation of the organ with cells of the organ recipient makes the organ more similar to the organ graft recipient, and therefore a graft of the organ is less likely to be rejected by the organ recipient Transplant organs or tissues having an immune component (for example, the lungs and intestines) normally go through a phase of immune deficiency between the time when the donor leukocytes are eliminated and the time when the recipient cells reconstitute the graft. However, grafts repopulated with recipient cells while within the surrogate animal are immune competent at the time of transplant. A decreased risk of GvHD, which would result from donor lymphocytes attacking the recipient's tissues and organs, is also attained.

The organs repopulated with recipient cells should be at decreased risk for rejection since the resident cells in those tissues are identical to the immunoreactive cells. The present invention provides repopulation of the donor organs which occurs outside of the recipient, in another animal. This offers multiple advantages over repopulation inside the recipient, including producing multiple organs and selecting the best animal, the use of fetal animals for adult recipients, and the use of techniques that are either impractical or unethical if performed in a human organ graft recipient. The invention also differs in that the organ graft has been repopulated prior to transplantation into the organ graft recipient, preventing the local immune deficiency that would occur if the organ donor cells were eliminated and replaced with recipient cells after transplantation.

Because of the severe shortage of human organ and tissue donors, transplant candidates have occasionally received xenografts for short term life support, referred to as bridge transplants, thereby providing additional time to locate a suitable human donor. Xenografts repopulated with human cells will be more readily accepted than an unaltered xenograft, although the xenografts repopulated with human cells are still subject to allogeneic rejection if the engrafted cells in the xenograft differ from the organ recipient. Xenografts repopulated with human cells in the course of surrogate tolerogenesis may be utilized as bridge transplants for human recipients that are genetically non-identical (allogeneic) to the source of the cells infused into the immune deficient surrogate.

For the ex vivo production of xenografts repopulated with organ graft recipient cells, the primary cellular targets of graft rejection include endothelial cells, monocytes, dendritic cells, and epithelial cells. A reaction against endothelium may lead to thrombosis, infarcts and irreversible destruction of the graft, particularly for heart, lung, liver, skin, and kidney grafts. The immune reaction against monocytes and related macrophages and dendritic cells may lead to innocent bystander injury of adjacent cells when enzymes and cytokines are released from the killed macrophages. Because the monocytes, macrophages, and dendritic cells are also APC and phagocytic cells, the monocytes, macrophages, and dendritic cells provide a major immune defense against infections, and the loss of the monocytes, macrophages, and dendritic cells may leave the graft, especially lung and intestinal grafts, susceptible to opportunistic infection.

The intestines are usually regarded as a digestive organ. However, the intestinal tract is also the largest lymphoid organ in the body. GvHD resulting from the resident lymphocytes attacking the organ graft recipient poses a major problem following transplantation of intestines. The GvHD resulting from the resident lymphocytes attacking the organ graft recipient has also been reported after liver transplantation, and is potentially a problem with lung transplants.

The above described problems from immune reactions may be avoided if the resident cells of the graft are replaced by organ graft recipient cells. After transplanting the organ into the organ graft recipient, the resident immune competent cells would consist of predominantly organ graft recipient cells, which would not react against the organ graft recipient.

The lymphoid cells normally residing in these tissues provide local protection against infectious agents. After transplant, however, the protective lymphocytes are often depleted, either because of rejection or immunosuppressive agents. Until the tissues are reconstituted with organ recipient cells, they are highly susceptible to infections.

The considerable risk of rejection of the organ graft normally makes repopulation of the organ graft by recipient cells within the recipient difficult. Because the organ graft recipient is dependent on the graft, the organ graft recipient is usually severely immune suppressed to delay or prevent rejection, which significantly slows down the repopulation process.

However, if the repopulation of the organ graft occurs in a surrogate, then the surrogate bears the risk of immune deficiency, and the organ graft recipient receives a graft already engrafted with the organ graft recipient's own cells, with decreased risk of rejection, infection, and GvHD.

Organ grafts repopulated with organ graft recipient cells is a byproduct of surrogate tolerogenesis as described above. However, the goals for optimal repopulation differ somewhat from the induction of tolerance and therefore the optimal method for a repopulated graft differs from the method of induction of tolerance. The generation of antigen specific suppressor cells and regulatory cells and factors is less important. The major goal of optimal repopulation is to achieve maximum engraftment with organ graft recipient cells and to achieve a reduction of resident surrogate cells.

Bone marrow transplantation is therefore preferable to intrauterine infusions for optimal repopulation. The chemotherapy and/or radiation selectively inhibits the regeneration of the surrogate endothelial cells, and eliminates precursor lymphocytes and macrophages. Bone marrow transplantation includes the potential advantage of having a controlled graft-vs-host reaction of the organ graft recipient cells against the surrogate cells. The engraftment of organ graft recipient endothelial cells and monocytic cells may be further enhanced by administering select growth factors; for example, endothelial cell growth factor may be used to enhance engraftment of organ graft recipient endothelial cells, and GM-CSF may be used to enhance engraftment of monocytic cells.

Transgenic surrogate animals carrying the marker gene KT (thymidine kinase) may also be used to enhance the repopulation of the organ graft with organ recipient cells. To enhance the engraftment of cell populations such as endothelial cells and dendritic cells, it would be advantageous to selectively injure the resident cells, creating space for engraftment by the organ recipient cells. For example, KT+ pigs may be produced where the KT is linked with a promoter gene for adhesion molecules such as ELAM or P-CAM. The KT would then be selectively expressed in cells such as endothelial cells. The corresponding fetal pigs are infused with human lymphocytes. After birth, the chimeric animals are treated with gancyclovir. This would lead to selective killing of the surrogate's endothelial cells which would then be replaced with KT- cells infused from the organ recipient.

The engraftment with organ graft recipient cells is best assessed by immunohistochemical studies of biopsies from the surrogate chimeras. Tissue sections are stained using antibodies specific for organ graft recipient endothelial cells; for example, human factor VIII; specific for leukocytes; for example, human CD45; and specific for surrogate endothelial cells and leukocytes. The relative numbers of organ graft recipient and surrogate cells are then scored.

Universal Surrogate Donor Animal

The organ graft recipient initially providing the cells for repopulation of the organ in the surrogate is the primary benefactor of grafts repopulated with organ graft recipient cells, but surrogate chimeras may also be useful for other human patients as bridge transplants. One potential disadvantage of surrogate tolerogenesis is that an organ cannot be provided immediately. A wait of two to seven months is typically required. This would not be practical for many settings such as someone with fulminant hepatitis and liver failure or after a massive myocardial infarct when a transplant would be needed immediately.

To provide tolerant lymphocytes and organs for emergency use, surrogate animals could be made chimeric with leukocytes from multiple members of the organ recipient species. For example, fetal pigs could be infused with leukocytes from multiple humans that express the most common histocompatibility antigens. The resulting chimeric pig would then be expected to contain suppressor cells that would suppress the reaction of human lymphocytes sharing class I or II HLA antigens with the organ recipient against any other human antigens resident in the chimeric pig. The transplant organs from these chimeric pigs would also be expected to be partially repopulated with cells from the organ recipient species (human). This would decrease the risk of rejection due to natural antibodies and cellular reactions to pig cells.

Liver Transplants as Bridge Transplants for Fulminant Hepatitis

Fulminant hepatitis with massive liver failure is a medical emergency that requires a liver transplant for survival. Porcine liver transplants have been used to provide temporary support until a human donor is found. For example, a organ graft recipient in hepatic failure was recently connected to a porcine liver for 4 hours, and, although only for a short time, the bridge transplant provided an extra 24 hours to locate a human donor to perform a human liver transplant. These xenografts rarely survive for more than a few hours, however. Livers that have been engrafted with unrelated human cells will survive longer than unmodified porcine livers. Using the present invention, a xenograft repopulated with human cells survives longer than an unaltered xenograft, even though the xenograft may eventually be rejected by an allogeneic reaction against the unrelated human cells.

Skin grafts

Porcine skin grafts are frequently done for the treatment of severe burns. However they are usually sloughed within a few days and serve more as dressings than tissue grafts. Skin from surrogate animals such as pigs that are modified as described above are more likely to engraft and provide more lasting benefit for the patient. Although the induction of specific immune tolerant suppressor cells in an immune deficient surrogate is not usually possible since most patients require skin grafting immediately, skin that has been repopulated with unrelated human cells is preferable to native pig skin. Lymphocytes and skin can also be provided from surrogates infused with multiple sources of cells. The induction of tolerance is also helpful for treatment of severe chronic skin disorders such as pemphigus vulgaris.

Organ grafts that are harvested from the surrogate for transportation to a remote facility should be perfused and placed in transport medium, in order to prevent ischemic changes. Solid organs removed from the chimera are usually perfused with mannitol and heparin prior to transplantation into the organ recipient, according to standard transplantation procedures for living donors. This helps to remove circulating surrogate cells from the organ and decrease the antigen disparity. Reconstituted solid organ grafts may be perfused with antibodies specific for surrogate cells and complement to remove surrogate cells from the graft. Additional preparation of organ graft may be performed as necessary. For example, pancreatic islets must be harvested from pancreas of the organ donor(s). Liver transplants are perfused with WU solution to delay ischemic changes.

In accordance with the above teaching, this invention provides isolated organs for allogeneic or xenogeneic transplant either as a bridge or permanent transplant, where the organs are repopulated with cells of the organ recipient and preserved for subsequent transplant and optionally for transportation. Preservation of organs for subsequent transplant is easily within the skill of the art. Preferably, the isolated organ according to this invention is treated to reduce the number of donor cells within the organ, for instance, by perfusion to flush out circulating cells or by perfusion with antibody and complement to destroy donor cells.

EXAMPLES

In order to facilitate a more complete understanding of the invention, experimental Examples are provided below. The following experiments demonstrate the principle of surrogate tolerogenesis as disclosed herein. However, the scope of the invention is not limited to specific embodiments disclosed in these Examples, which are for purposes of illustration only.

EXAMPLE 5

Production of human-pig chimeras

In initial experiments, human cord blood or adult peripheral blood lymphocytes were infused into fetal pigs at 50 days gestation (estimated body weight 100 grams). The cells were injected by externalizing the uterus through an abdominal incision in the sow which was under general anesthesia. The ultrasound transducer was placed on the surface of the uterus and a suspension of cells injected into the fetal pig abdomen. The transplant infused approximately $1 \times 10^8$ cells/ kilogram body weight (kg bw). Sutures were placed on the uterus over the injected fetal pig to identify different experimental groups.

Postoperatively, the sow received progesterone and antibiotics to prevent premature contractions and infections. The fetal pigs were followed approximately 4 weeks later with ultrasound, assessing fetal growth and viability. The piglets were delivered 35 days post-transplant by Cesarian section. Cord blood was collected. The pigs were weighed, their crown-rump length determined and they were examined for evidence of GvHD. Most of the piglets were euthanized by exsanguination. The cord blood and lymphoid tissues were examined by flow cytometry, immunohistochemistry, and histology. Flow cytometry employed monoclonal antibodies to human CD45, CD4 and CD8. Immunohistochemistry studies included alkaline phosphatase studies for human CD45.

Six of 8 injected piglets demonstrated human chimerism in the peripheral blood and lymph nodes. $CD4^+$ and $CD8^+$ lymphocytes were detected by flow cytometry. None of the piglets demonstrated evidence of GvHD. They were all normal weight and length for this stage of gestation.

EXAMPLE 6

Production of chimeric pigs

A second experiment used the same procedure as Example 5, except that human cells were infused into fetal pigs at an earlier stage of development (42 days gestation) in order to enhance the amount of chimerism. At this time, the pigs were much smaller (estimated body weight 10 gram) and at a significantly earlier stage in the development of the immune system. The first litter injected at this stage was totally aborted. Autopsies testing for the cause of the abortion showed primarily trauma. In a second litter transplanted with $4 \times 10^8$ and $4 \times 10^9$ cells/kg bw, the three pigs transplanted with high cell dose died shortly after transplant, while of the three transplanted at a lower dose, one was healthy at delivery, and one lived for a short time. The effect of cell dose on survival was thought to be due to GvHD.

The surviving fetal pig (delivered at 95 days) had no evidence of GvHD but showed 10% human chimerism in the bone marrow, 8% human chimerism in the peripheral blood, and 6% human chimerism in the spleen. Fifty percent of the lymphocytes were single positive CD4 cells. Immune alkaline phosphatase stains showed numerous human cells in the cortex of the thymus and scattered human cells in the thymic medulla. Based on total splencytes, it is estimated that the number of human cells in this fetal pig had increased at least 10-fold since the injection.

Subsequent transplants usually limited the total number of T cells to less than $2 \times 10^8$ T cells/kg bw. However, we have subsequently transplanted 24 fetal piglets in 3 sows with 1 to $4 \times 10^9$ cells/kg bw (using cells from 4 human "patients"), and we have not seen any more abortions due to GvHD. Ultrasound follow-up in the most advanced litter (at 100 days) has shown all identified fetal pigs to be viable and normal size for this stage of gestation. One piglet delivered at term showed 29% human lymphocytes in the cord blood, but no evidence of GvHD.

These studies demonstrate that human cells proliferate and differentiate within fetal pigs. Better engraftment was evident when the human "patient" lymphocytes and stem cells were infused at an earlier stage of development, at about 42 or 43 days gestation, representing the start of the second trimester. This resulted from an increase in the cell infusion per unit body weight because the fetus was much smaller (10%) as well as an earlier stage of immune ontogeny. Therefore, the infused cells did not need to compete with the resident lymphocytes. Although it generally appears preferable to infuse the human hematopoietic and lymphopoietic cells at an earlier stage, later infusion could still be useful when it would be important to minimize the waiting period between the initial infusion and the organ xenograft.

EXAMPLE 7

Suppressor cells in chimeric pigs

Chimeric cells from the fetal pigs of the initial infusion (described in Example 5, low dose human lymphocytes) and from the surviving piglet from the higher dose transplant (described in Example 6, $4 \times 10^8$ cells/kg bw, 10% marrow chimerism) were subsequently tested for suppressor cells and for antigen specificity of the suppression. Additionally, chimeric cells from the piglet receiving the higher dose transplant (Example 6) were tested for the relative frequency of suppressor cells.

The overall immune reactivity was established by comparing two-way mixed lymphocyte reactions (MLRs) with the corresponding autologous reactions. Chimeric piglet cells ($10^5$ cells) were reacted with human lymphocytes ($10^5$ cells) from the patient or unrelated controls. After six days of incubation, tritiated thymidine was added and the incorporation determined. The incorporation was compared to the sum of the thymidine incorporation in autologous reactions.

Suppression of immune reactivity was assayed by comparing the two-way MLRs ($10^5$ cells from the chimera mixed with $10^5$ fresh human lymphocytes from either the patient or unrelated human control subjects) with the sum of the one-way MLRs (thymidine incorporation by a mixture of chimeric cells and irradiated human cells plus thymidine incorporation by a mixture of human cells and irradiated chimeric cells). The MLRs were performed in standard fashion, incubating the cells at 37° C., 5% $CO_2$. At the end of 6 days, tritiated thymidine was added to the culture, the lymphocytes collected and washed on a filter, and the incorporation determined. In order to assess relative antigen specificity of suppression, the suppressor cell assays were compared to suppressor cell assays based on chimeric cells mixed with unrelated human cells or "patient" cells mixed with unrelated pig cells. Control assays also included autologous reactions.

Figure 4:
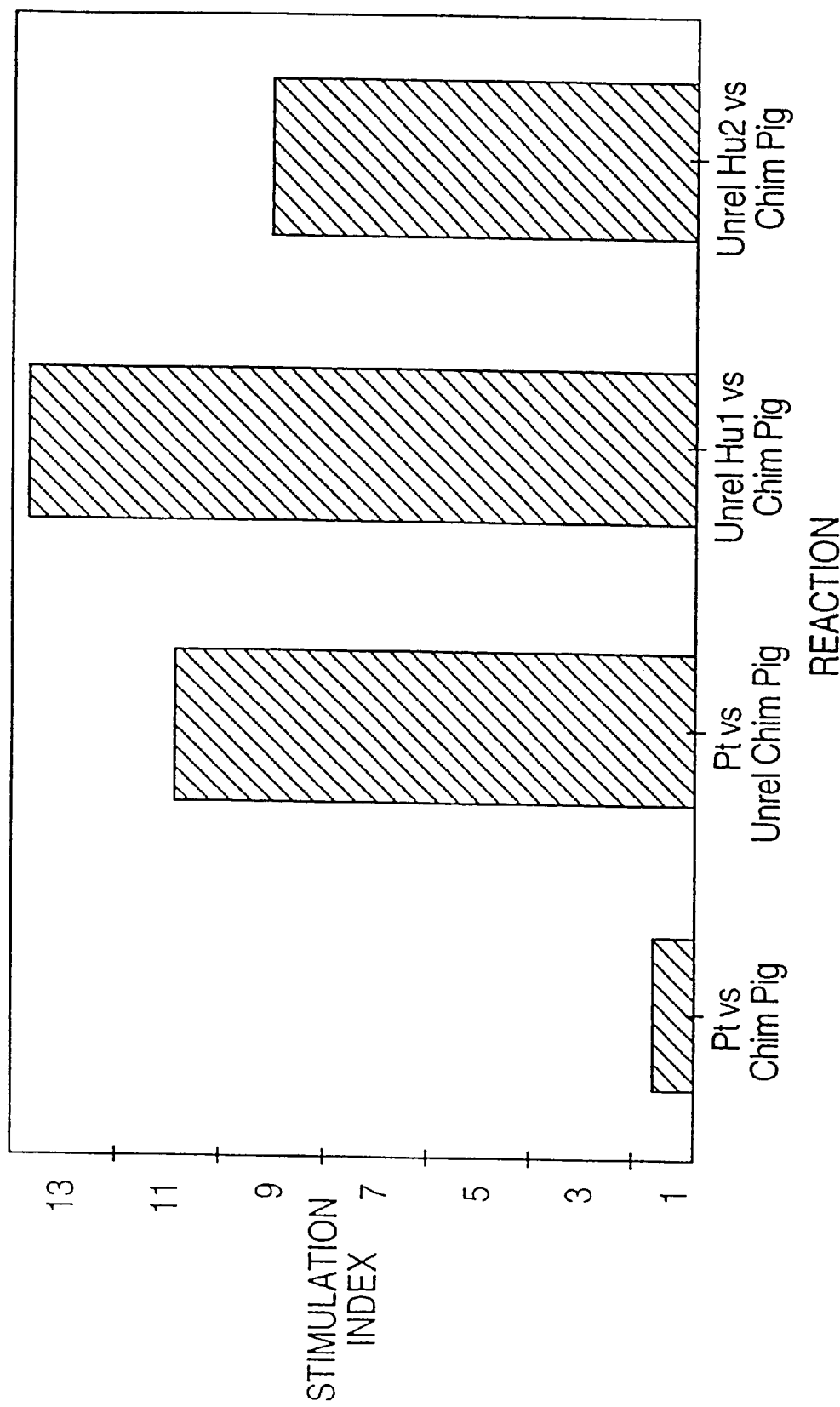
FIG. 4 shows two-way mixed lymphocyte reactions between human cells and cells from one of two pigs. No immune stimulation of the lymphocytes occurs when the cells are from the human "patient" and a chimeric pig which had been infused with patient cells in utero, but stimulation does occur when either patient cells or chimeric pig cells are exposed to cells from an unrelated pig or human, respectively.

Extensive immunology studies were performed with the surviving piglet from the transplant described in Example 6, which demonstrated 10% human chimerism in the marrow (8% in the peripheral blood, 6% in the spleen). As shown in FIG. 4, there was minimal immune reactivity in the two-way MLR containing fresh human "patient" cells and chimeric cells, compared with the autologous controls. In contrast, when the patient's cells were reacted with unrelated pig cells or the chimeric cells were incubated with unrelated human cells, there were vigorous reactions (SI greater than 9.13).

Figure 5:
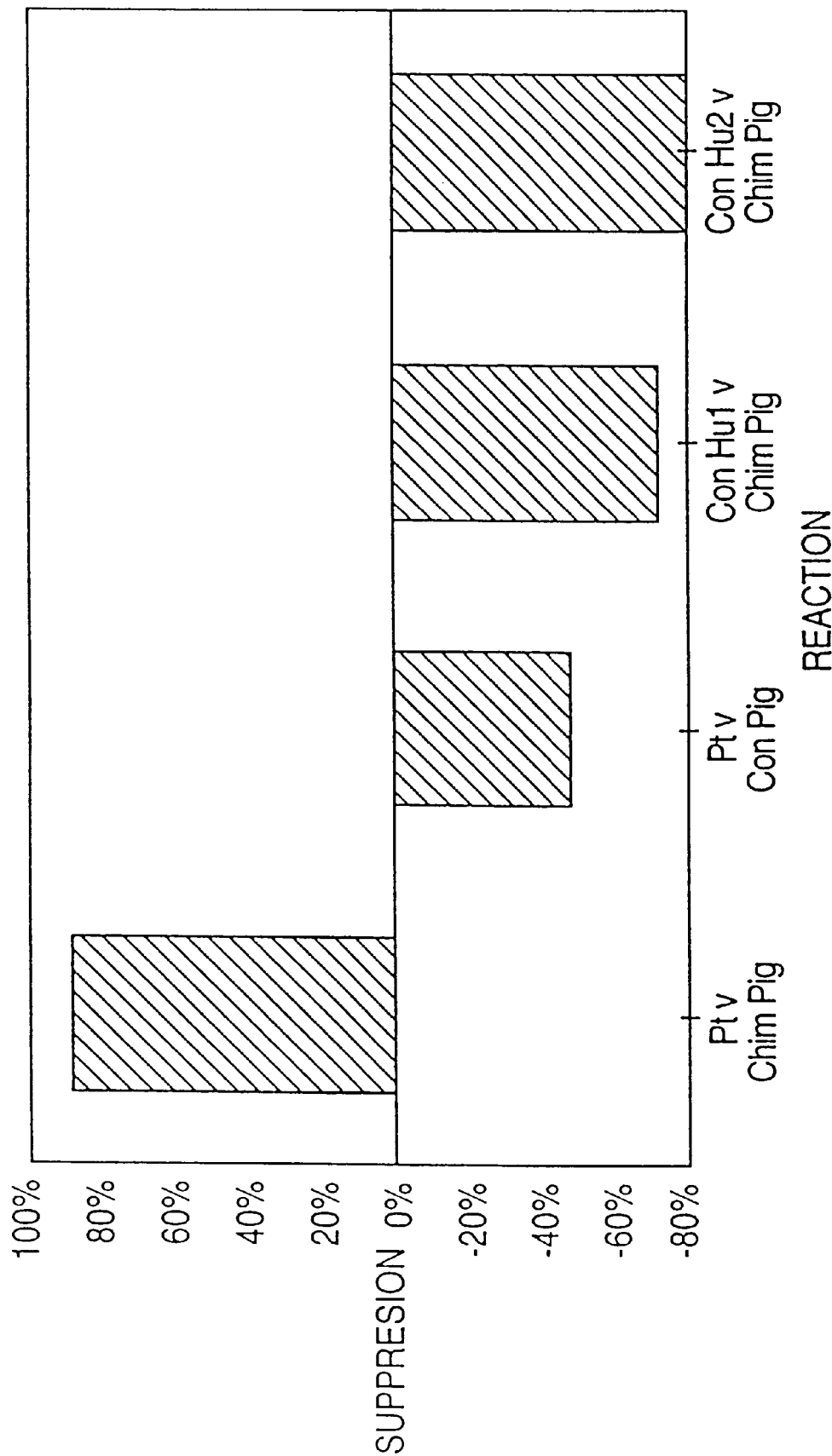
FIG. 5 shows the results of the two-way mixed lymphocyte reactions (MLR), displayed as suppression. Again, the two-way MLR between cells from the human "patient" and cells from the chimeric pig exposed in utero are suppressed (87% relative to one-way reactions), while the two-way MLR reactions between either cell population and cells of an unrelated pig or human, respectively, are stimulated.

Immune suppression was assayed by comparing the two-way MLR with the sum of the corresponding one-way MLRs (either pig or human cells irradiated). As evident from FIG. 5, the two-way MLR with chimeric pig and patient cells showed 87% suppression. In contrast, the patient cells with unrelated pig cells or the chimeric pig cells with unrelated human cells demonstrated stimulation rather than suppression. These studies demonstrate that cells produced within the chimeric pig effectively suppress the ability of fresh human lymphocytes from the "patient" to mount an immune response stimulated by the antigens of the chimeric pig.

Figure 6:
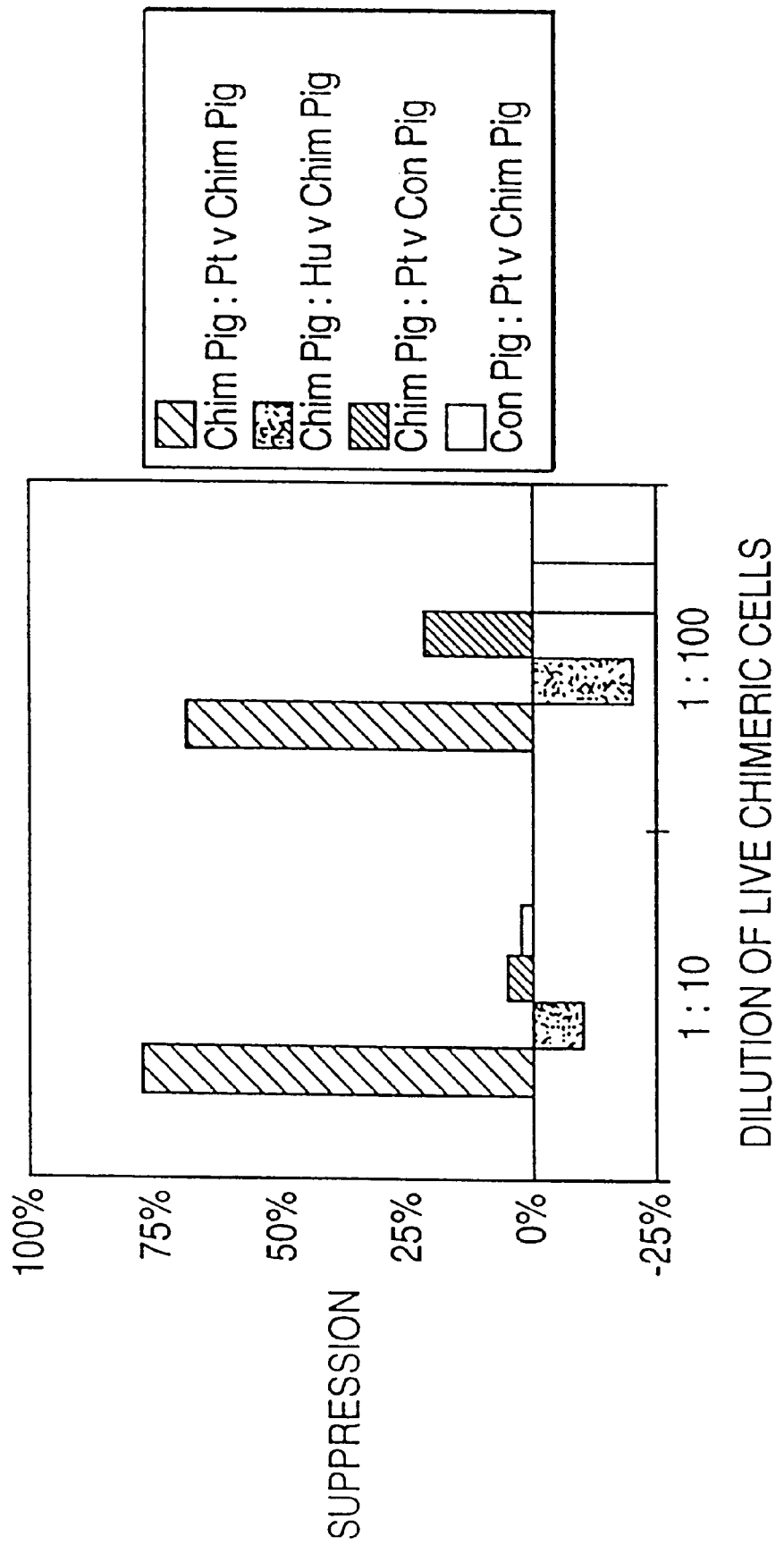
FIG. 6 shows that the chimeric pig's lymphocytes suppress the MLR, even at a dilution of 1:100.

As an indication of the relative frequency of suppressor cells in the chimeric pigs, viable chimeric cells were added at various dilutions to a one-way MLR (reacting fresh human cells with irradiated chimeric cells). The results are shown in FIG. 6. Even when the viable chimeric cells were diluted to 1 to 100, 70% suppression of the MLR was observed. In contrast, there was minimal suppression of the MLR between the patient and unrelated pig cells and no detectable suppression between unrelated humans and the chimeric pig.

The studies in this Example demonstrate that cells produced within the chimeric pigs effectively block the reaction of fresh human lymphocytes from the "patient" to the corresponding pig antigens. This suppression appears to be antigen specific, and suppressive moieties appear to be present in high numbers. A small number of suppressor cells from the surrogate pig can transfer tolerance to the human patient and prevent the reaction of human lymphocytes as well as the chimeric pig lymphocytes to the pig antigens. Because the suppression is relatively specific, the adoptive transfer should not lead to significant immune deficiency and should not put the patient at significant risk for infection or malignancy.

EXAMPLE 8

Relative antigen-specific suppression between littermates

Figure 7:
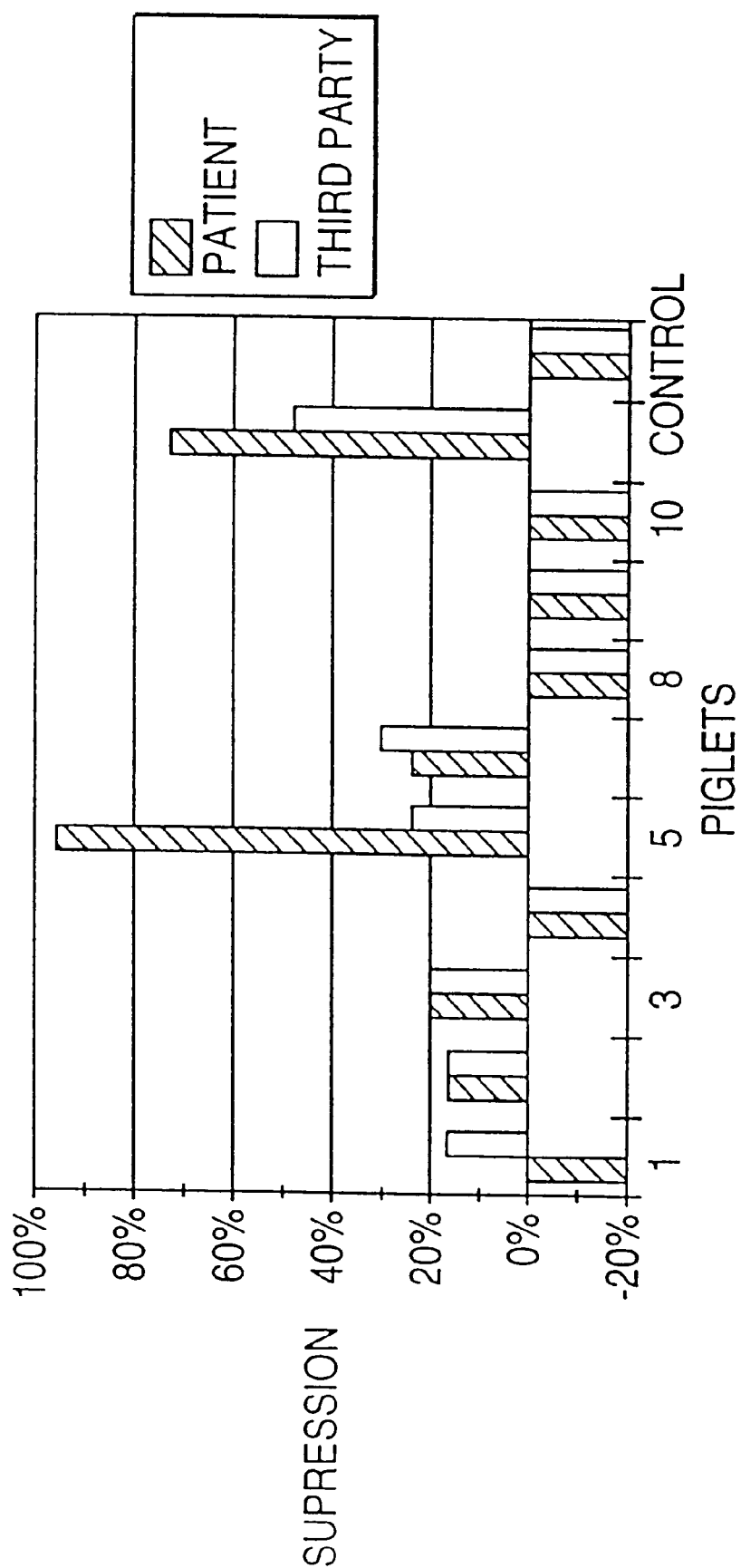
FIG. 7 shows the suppressive activity of lymphocytes from an entire litter of pigs exposed in utero to human lymphocytes. The results show variation between littermates, indicating the benefit of screening to select the individual chimeric pig providing the greatest level of immune suppression.

The results of suppression studies on eleven piglets from a single litter are shown in FIG. 7. Suppression of the MLR between cells from each individual piglet and cells from either the "patient" or an unrelated human was tested, as described for Example 7. As shown in FIG. 7, piglet Nos. 5 and 11 showed suppression of immunoreactivity, but only for piglet No. 5 was this suppression specific for the antigens and cells of the "patient" who served as the source of cells for fetal infusion.

These studies confirmed similar findings seen in the initial study with limited human chimerism. Of three recipients of human cord blood, peripheral blood from one chimeric piglet demonstrated minimal reactivity with the corresponding "patient" lymphocytes but normal reactivity to two unrelated human subjects. When the two way MLR was compared with the corresponding one way MLR's, there was 97% suppression of the reaction. This also suggests that the cells responsible for suppression are radiosensitive. Two other recipients showed only 50% suppression.

CLA

The assays performed on the piglets with limited chimerism illustrates the advantage of selection. When a patient is transplanted, the success or failure depends on the development of tolerance within that one patient. With surrogate tolerogenesis, however, multiple fetuses can be transplanted and the fetus exhibiting the greatest tolergenic effect selected. Clearly, piglet No. 5 of this Example or the first pig of Example 6, would be superior to the other piglets in the litters. In a clinical situation, the lymphocytes from these pigs, and the corresponding organ grafts, would be utilized.

EXAMPLE 9

Chimeric organ repopulation

Repopulation of organs of the surrogate animal with human cells has been demonstrated. Fresh frozen sections of skin and thymus from the piglet with 10% marrow chimerism from Example 6, were evaluated by immunohistochemistry. ImmunoaLkine phosphatase stains for human common leukocyte antigen (CD45) were performed. Control specimens included specimens from pigs that were not infused with human cells.

Sections of skin showed human CD45+ cells in the region of vascular endothelial cells. Dendritic cells were positive for human CD45 in the dermis. Sections of thymus from the chimeric pig showed human CD45+ dendritic cells within the medulla. In addition, many of the thymocytes stained for human CD45. This staining was not evident in pigs that had not been infused with human cells. Thus, when tissues of the chimeric pig were examined, the tissues (skin and thymus) were partially repopulated with human leukocytes.

EXAMPLE 10

Suppressor cells induced in the surrogate animal in vivo

Immune challenge represents an in vivo test of immune tolerance and suppressor cells. If the surrogate animal is tolerant to the patient and contains suppressor cells that block the reaction of fresh patient lymphocytes to the surrogate animal, then a large infusion of fresh patient cells should lead to an increase in chimerism without significant GVHD. On the other hand, if the surrogate animal is not tolerant to the patient, then the patient's cells will be rejected. If the surrogate animal is tolerant to the patient, but does not contain suppressor cells, then the fresh lymphocytes would engraft but produce graft-vs-host disease.

The immune challenge was performed as follows. Upon the birth of LEW rats, C57B⅙ mouse marrow cells were injected i.p. into the newborn rats (less than 24 hours old). At eight weeks of age, the rats contained approximately 0.5% mouse cells (Ly5+) in the peripheral blood. The chimeric rats were injected with either $4\times10^7$ mouse marrow cells, $4\times10^7$ mouse splenocytes, or vehicle i.p. Two weeks later, the blood was assessed for mouse cells (Ly5+). Skin biopsies were taken for assessment of GVHD.

Figure 8:
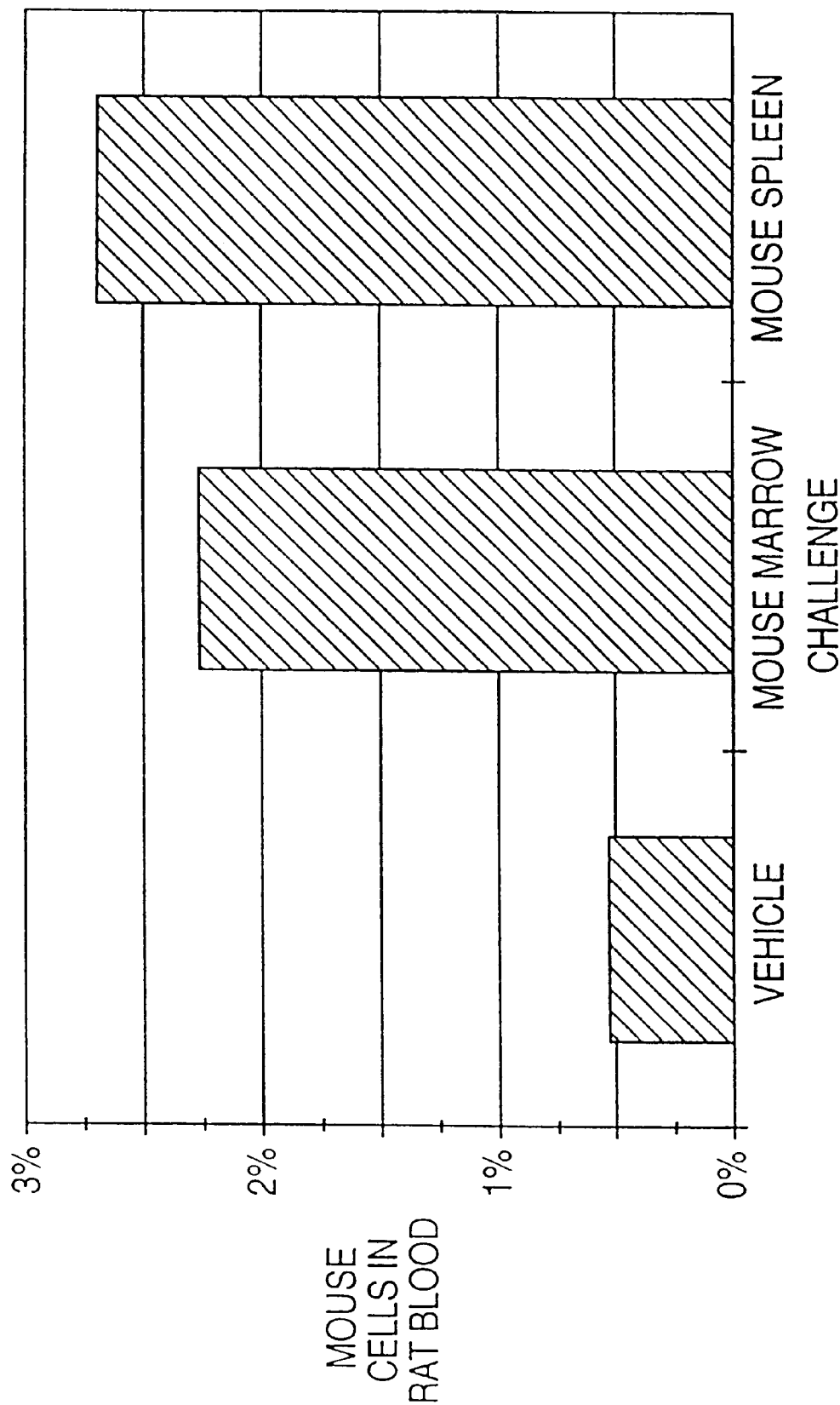
FIG. 8 demonstrates the presence of suppressor cells in chimeric surrogates by in vivo tests of immune tolerance. Challenge of chimeric rats with fresh mouse lymphocytes results in an increase in the number of mouse cells in the rats. Immune tolerance in the chimeric rat suppresses both rejection by the rat immune system and graft-vs-host reaction by the newly introduced mouse lymphocytes.

The infusion of fresh marrow or splenocytes led to a 5 to 10 fold increase in mouse cells in the peripheral blood of the rats (see FIG. 8). Skin biopsies showed no evidence of GVHD. The chimeric rats continued to gain weight.

This experiment provides an in vivo demonstration of suppressor cells in the chimeric rat surrogate. Had the chimeric rats not had any suppressor cells, the engraftment of fresh mouse cells should have led to GVHD. The infused mouse cells were not rejected and did not cause GVHD. Indeed, the relative number of mouse cells increased 5 to 10 fold. This procedure also demonstrates that the chimerism may be enhanced without GVHD. Thus, potentially there could be an expansion of the suppressor cells in the surrogate.

It will be apparent to those skilled in the art that various modifications may be made to the methods of surrogate tolerogenesis of the instant invention without departing from the scope or spirit of the invention, and these modifications and variations are within the contemplation of this invention provided they come within the scope of the appended claims and their equivalents.

I claim:

1. A method for xenograft transplant of an organ to a recipient mammal from a donor mammal, wherein said recipient has increased immuno tolerance to donor tissue, comprising the steps of:
   a) collecting a first cell population from the recipient, said first cell population containing lymphocytic progenitor cells, wherein at least a portion of cells that are specifically cytotoxic to tissue from a surrogate animal are removed from said first cell population;
   b) administering said first cell population to said surrogate, said surrogate being in a state of immune deficiency;
   c) developing in said surrogate a state of immune competence;
   d) collecting from said immune competent surrogate a second population of cells, said second cell population containing immunocompetent cells, said immunocompetent cells specifically suppressing immune response of said recipient to tissue of said surrogate;
   e) infusing said second population of cells into said recipient;
   f) excising an organ from a donor mammal wherein the donor mammal is selected from the group consisting of the same surrogate mammal, the same inbred strain as the surrogate mammal and a littermate of the surrogate mammal; and
   g) transplanting said organ into said xenograft recipient.

2. The method of claim 1, wherein said first cell population from the recipient comprises bone marrow cells.

3. The method of claim 1, wherein said surrogate is a fetal mammal or a neonatal mammal.

4. The method of claim 1 further comprising treating said recipient with an immunosuppressive agent before transplanting said organ into said xenograft recipient.

5. The method of claim 1, wherein said second population of cells comprises spleen cells.

6. The method of claim 1, wherein the organ from the donor animal comprises vascular tissues.

7. The method of claim 1 wherein the said donor mammal is the same inbred strain as the surrogate mammal.

8. The method of claim 1 wherein the said donor mammal is a littermate of the surrogate mammal.

9. A method of transplanting an organ from a donor mammal to a recipient mammal which is not syngeneic with said donor mammal, comprising
   a) administering to said recipient mammal a cell population containing immunocompetent cells specifically suppressing immune response of said recipient mammal to said donor mammal, wherein said cell population is obtained from a surrogate mammal, said surrogate mammal being a chimeric animal containing lymphocytes derived from said recipient mammal; and
   b) transplanting an organ from said donor mammal to said recipient mammal, wherein said donor mammal is selected from the group consisting of the same surrogate mammal, the same inbred strain as the surrogate mammal, and a littermate of the surrogate mammal,
   whereby immune response of said recipient mammal to said organ is reduced as compared to the immune response of said recipient mammal in the absence of the administration of said surrogate mammal cell population.

10. The method of claim 9, wherein said surrogate mammal and said recipient mammal are from different species.

11. The method of claim 10, wherein said surrogate mammal and said donor mammal are different individual mammals.

12. The method of claim 10, wherein said donor mammal and said recipient mammal are from the same species.

13. The method of claim 9, wherein said donor mammal is mature when said surrogate mammal is born.

14. The method of claim 9, wherein said donor mammal and said surrogate mammal are different individuals and said organ is a population of cells, further wherein said cell population is expanded by culturing in said surrogate mammal before transplanting into said recipient mammal.

15. The method of claim 14, wherein said organ is selected from the group consisting of pancreatic islet cells and hepatic cells.

16. The method of claim 14, wherein said organ is bone marrow.

17. A method of transplanting an organ from a third party donor mammal to a recipient mammal which is of the same species as said third party donor mammal, comprising
   a) administering to said recipient mammal a cell population containing immunocompetent cells specifically suppressing immune response of said recipient mammal to said third party donor mammal, wherein said cell population is obtained from a surrogate mammal, said surrogate mammal being a chimeric mammal containing lymphocytes derived from a set of mammals of the same species as the recipient, said set of mammals having a plurality of tissue types; and
   b) transplanting an organ from said third party donor mammal to said recipient mammal,
   whereby immune response of said recipient mammal to said organ is reduced as compared to the immune response of said recipient mammal in the absence of the administration of said surrogate mammal cell population.

18. A kit for suppression of immune rejection by a recipient mammal of an organ transplanted from a third party donor mammal which is of the same species as the surrogate mammal comprising an immune suppressive composition comprising a cell population obtained from a surrogate mammal, said surrogate mammal being a chimeric mammal containing lymphocytes derived from said recipient mammal and expressing antigens substantially identical to said third party donor mammal, and said cell population containing immunocompetent cells specifically suppressing immune response of said recipient mammal to said third party donor mammal, said cell population being suspended in a medium suitable for injection into said recipient mammal.

19. The kit of claim 18, wherein said immune suppressive composition is substantially free of immune reactive cells of said surrogate.

20. The kit of claim 18, wherein the composition suitable for injection into said recipient mammal is free of infectious agents.

21. A kit for organ transplant into a recipient mammal comprising an excised bodily organ from a surrogate mammal wherein said surrogate is different from said recipient and perfusion solution in an amount sufficient to preserve said excised organ in condition suitable for transplant into said recipient mammal, wherein a plurality of resident cells of said organ are cells from the same species as said recipient, said resident cells being selected from endothelial cells, monocytes, dendritic cells, and lymphoid cells, said bodily organ being placed in the perfusion solution and preserved in condition suitable for transplant into said recipient mammal.

22. The kit of claim 21, wherein said plurality of resident cells are syngeneic with said recipient mammal.

23. A method of preparing an excised organ of claim 21 for transplant into a recipient mammal which is not syngeneic with said excised organ, comprising:
   a) collecting a cell population from said recipient mammal, said first cell population containing lymphocytic progenitor cells;
   b) administering said cell population to a surrogate mammal, said surrogate being in a state of immune deficiency;
   c) developing in said surrogate a state of immune competence;
   d) excising from said immune competent surrogate an organ, said organ being populated with at least a plurality of cells derived from said recipient mammal; and
   e) placing said organ in perfusion solution so that said excised organ is preserved in condition suitable for transplant into said recipient mammal.

24. The method of claim 23, further wherein at least a portion of cells that are specifically cytotoxic to tissue from said surrogate mammal are removed from said cell population before said cell population is administered to said surrogate.

25. A method of preparing an excised organ for transplant into a recipient mammal which is not syngeneic with said excised organ, comprising:
   a) collecting a cell population from an animal which is of the same species as said recipient mammal, said cell population containing lymphocytic progenitor cells;
   b) administering said cell population to a surrogate mammal, said surrogate being in a state of immune deficiency;
   c) developing in said surrogate a state of immune competence;
   d) excising from said immune competent surrogate an organ, said organ being populated with a plurality of cells derived from said recipient mammal; and
   e) placing said organ in perfusion solution so that said excised organ is preserved in condition suitable for transplant into said recipient mammal.

26. The method of claim 25, further wherein at least a portion of cells that are specifically cytotoxic to tissue from said surrogate mammal are removed from said cell population before said cell population is administered to said surrogate.

27. The method of claim 25, wherein lymphocytes derived from a set of mammals of the same species as the recipient are administered to said surrogate mammal while it is in a state of immune deficiency, said set of mammals having a plurality of tissue types.

28. The method according to claim 27, wherein said recipient mammal is a human having severe burns, said surrogate mammal is a non-human mammal, and said organ is a graft of skin from said non-human mammal for application to the burned area of said recipient, wherein a plurality of resident cells of said skin are cells derived from the same species as said patient.

29. The method of claim 25, wherein said donor mammal and said surrogate mammal are different individuals and said organ is a population of cells, further wherein said cell population is expanded by culturing in said surrogate mammal before transplanting into said recipient mammal.

30. The method of claim 29, wherein said organ is selected from the group consisting of pancreatic islet cells and hepatic cells.

31. The method of claim 29, wherein said organ is bone marrow.

32. A method of therapy for a patient having fulminant hepatitis, comprising periodically transplanting hepatic cells prepared according to claim 30 into said patient so long as hepatic necrosis continues.

33. A method of suppressing specific immune response of a recipient human to a transplantable organ of a non-human mammal comprising administering to the recipient human, prior to transplantation of the organ of a non-human mammal, a cell population containing immunocompetent cells specifically suppressing immune response of the recipient human to the organ of the non-human mammal, the cell population being obtained from a non-human surrogate mammal, the non-human surrogate mammal being a chimeric animal containing said immunocompetent cells specifically suppressing human immune response to cells from the non-human mammal, the said immunocompetent cells being derived from the recipient human, whereby immune response of the recipient human to the organ is reduced as compared to the immune response of said recipient mammal in the absence of the administration of said surrogate mammal cell population.

34. The method of claim 33, further wherein at least a portion of cells that are specifically cytotoxic to tissue from said surrogate mammal are removed before cells are administered to said surrogate.

35. The method of claim 33, further comprising, before the step of collecting said cell population, a step of collecting fresh lymphocytes from said recipient and infusing said fresh lymphocytes into said developed surrogate.

36. The method of claim 33, wherein said surrogate is a fetal mammal.

37. The method of claim 33, wherein the surrogate is selected from the group consisting of a newborn mammal, a juvenile mammal and an adult mammal, said mammal having received lethal irradiation or chemotherapy followed by bone marrow transplant of a cell population comprising hematopoietic and lymphoid cells from an organism selected from said recipient mammal, said donor mammal, and said surrogate, or a mixture of hematopoietic and lymphoid cells from two or more of these organisms.

38. The method of claim 33, wherein said surrogate is the same mammal as said donor mammal.

39. The method of claim 33, wherein said lymphocytes are additionally administered to a plurality of immune deficient surrogates and said plurality of surrogates is allowed to develop into immune competent organisms.

40. The method of claim 39, further comprising, before the step of collecting said cell population of claim 17, the steps of:
  i) collecting respective blood or spleen samples from the plurality of immune competent developed surrogates;
  ii) testing the respective blood samples to determine a degree of engraftment with cells of said recipient mammal and to determine a degree of maturation of lymphocytes in the respective blood samples;
  iii) testing respective cells of the plurality of developed surrogates for specific suppression of immune reactivity between recipient mammal cells and donor mammal cells;
  iv) selecting, in response to the steps of testing the respective blood samples, a selected set of the plurality of developed surrogates, said selected set having the greatest degree of engraftment and the greatest immune suppression;
  v) testing for graft-vs-host disease (GvHD) against respective developed surrogates of the selected set by collecting fresh lymphocytes from said xenograft recipient and infusing said fresh lymphocytes into the selected set of developed surrogates; and
  vi) identifying a best developed surrogate from the selected set of developed surrogates, based on least degree of GvBD in response to infusion of lymphocytes from the xenograft recipient.

41. The method of claim 33, wherein lymphocytes derived from both genetic parents of said donor mammal are administered to said surrogate mammal while it is in a state of immune deficiency.

42. The method of claim 41, wherein said organ is a cell suspension, and further wherein the cell suspension contains cells from more than one off-spring of said genetic parents.

43. The method of claim 41, wherein said donor mammal is mature when said surrogate mammal is born.

44. The method of claim 33, wherein said donor mammal and said surrogate mammal are different individuals and said organ is a cell suspension, further wherein said cell suspension is expanded by culturing in said surrogate mammal before transplanting the expanded cell suspension into said recipient mammal.

45. The method of claim 44, wherein said organ is selected from the group consisting of pancreatic islet cells and hepatic cells.

46. The method of claim 44, wherein said organ is bone marrow.

47. The method of claim 33, wherein the immunocompetent cells are human lymphocytes derived from hematopoietic cells of the recipient human introduced into the surrogate animal when the surrogate mammal was in a state of immune deficiency, the immunocompetent cells being collected from the surrogate mammal after the surrogate mammal achieved a state of immune competency.

48. The method of claim 33, wherein the non-human surrogate mammal is a primate, an artiodactyl or a carnivore.

49. The method of claim 33, wherein the non-human surrogate mammal is a primate or a pig.

50. The method of claim 33, wherein the non-human surrogate mammal is a rodent or a lagomorph, and the transplantable organ is a suspension of cells.

51. A method of preparing an excised non-human organ suitable for transplant into a recipient human comprising:
  a) collecting a human cell population containing lymphocytic progenitor cells;
  b) administering the cell population to a non-human donor mammal, the mammal being in a state of immune deficiency;
  c) developing in the non-human mammal a state of immune competence;
  d) excising an organ from the immune competent non-human mammal, the organ being populated with a plurality of cells derived from the human cell population; and
  e) placing the organ in perfusion solution so that the excised organ is preserved in condition suitable for transplant into a recipient human.

52. The method of claim 51, wherein the non-human mammal is a primate, an artiodactyl or a carnivore.

53. The method of claim 51, wherein the non-human surrogate mammal is a primate or a pig.

54. The method of claim 53, wherein the non-human mammal in a state of immune deficiency is a fetal mammal.

55. The method of claim 51, wherein the human cell population is obtained from the recipient human.

* * * * *

UNITED STATES PATENT AND TRADEMARK OFFICE
CERTIFICATE OF CORRECTION

PATENT NO.  : 6,060,049
DATED       : May 9, 2000
INVENTOR(S) : William E. Beschorner It is certified that error appears in the above-identified patent and that said Letters Patent is hereby corrected as shown below:

Claim 27, Column 45,
Line 8, "17" has been replaced with --33--.
Line 33, "GvBD" has been replaced with --GvHD--.

Signed and Sealed this

Nineteenth Day of June, 2001

*Attest:*

*Attesting Officer*

NICHOLAS P. GODICI
*Acting Director of the United States Patent and Trademark Office*